(12) United States Patent
Petkovich et al.

(10) Patent No.: US 8,574,862 B2
(45) Date of Patent: Nov. 5, 2013

(54) METHODS AND COMPOSITION FOR MEASURING THE AMOUNT OF VITAMIN D DERIVATIVES

(75) Inventors: P. Martin Petkovich, Kingston (CA); Christian F. Helvig, Markham (CA)

(73) Assignee: Cytochrama Inc., Markham, Ontario (CA)

( * ) Notice: Subject to any disclaimer, the term of this patent is extended or adjusted under 35 U.S.C. 154(b) by 0 days.

(21) Appl. No.: 13/318,442

(22) PCT Filed: May 3, 2010

(86) PCT No.: PCT/IB2010/001123
§ 371 (c)(1),
(2), (4) Date: Dec. 21, 2011

(87) PCT Pub. No.: WO2010/128393
PCT Pub. Date: Nov. 11, 2010

(65) Prior Publication Data
US 2012/0094396 A1    Apr. 19, 2012

Related U.S. Application Data

(60) Provisional application No. 61/175,919, filed on May 6, 2009.

(51) Int. Cl.
*G01N 33/53* (2006.01)
(52) U.S. Cl.
USPC .......................................................... 435/7.8
(58) Field of Classification Search
None
See application file for complete search history.

(56) References Cited

U.S. PATENT DOCUMENTS 6,689,574 B1    2/2004    Cummings et al.
2011/0177611 A1*  7/2011   Schwahn et al. .............. 436/501

FOREIGN PATENT DOCUMENTS

EP          0583945  A2    2/1994
WO    WO-2008/092917  A1    8/2008

OTHER PUBLICATIONS

De et al., Novel biosensors for the detection of estrogen receptor ligands, *J. Ster. Biochem. Molec. Biol.*, 96(3-4): 235-44 (2005).
Issa et al., Molecular mechanism of vitamin D receptor action. *Inflamm. Res.*, 47(12): 451-75 (1998).
Kristjansson et al., Two mutations in the hormone binding domain of the vitamin D receptor cause tissue resistance to 1,25 dihydroxyvitamin D3, *J. Clin. Invest.*, 92: 12-16 (1993).
Nayeri et al., Functional conformations of the nuclear 1 alpha,25-dihydroxyvitamin D3 receptor. *Biochem J.*, 327: 561-8 (1997).
Racz et al., Hormone-dependent translocation of vitamin D receptor is linked to transactivation, *J. Biol. Chem.*, 274(27): 19352-60 (1999).
Reschly et al., Functional evolution of the vitamin D and pregnane X receptors, *BMC Evol. Biol.*, 7: 222 (2007).
Rochel et al, the crystal structure of the nuclear receptor for vitamin D bound to its natural ligand. *Mol. Cell.*, 5(1): 173-9 (2000).
Stafslien et al., Analysis of ligand-dependent recruitment of coactivator peptides to RXRbeta in a time-resolved fluorescence resonance energy transfer assay, *Molec. Cell. Endocrinol.*, 264(1-2): 82-9 (2007).
Yamamoto et al., Three-dimensional structure-function relationship of vitamin D and vitamin D receptor model. *Steroids*, 66: 177-87 (2001).
International Search Report and Written Opinion of the International Searching Authority, European Patent Office, issued in connection with International Application No. PCT/IB2010/001123, dated Sep. 21, 2010.

* cited by examiner

*Primary Examiner* — Michael Pak
(74) *Attorney, Agent, or Firm* — Marshall, Gerstein & Borun LLP

(57) ABSTRACT

Methods and compositions for measuring the amount of vitamin D derivatives are disclosed. Fluorescence Resonance Energy Transfer (FRET) in combination with a modified ligand-binding domain of the vitamin D receptor (LBD-VDR) to measure vitamin D derivatives are also disclosed.

10 Claims, 7 Drawing Sheets

Figure 1A

A. DNA-binding domain

```
PXR_human       QICRVCGDRATGYHFNVTCEGCKGFFRRAMKRNARLRCPFRKGACEITRKTRRQCQACR
PXR_chicken     KVCAVCGDRATGYHFRVNSCEGCKGFFRRSILRSYHFTCPF-TRSCPITKARRRQCQACR
PXR_fugu        RACGVCGDQARGYHFNAWTCEGCKGFFRRAIKRTPPLPCQF-LNKCSITKRNRRQCQDCR
VDR_human       RTCGVCGDRATGFHFNAMTCEGCKGFFRRSMKRKALFTCPFN-GDCRITKDNRRHCQACR
VDR_mouse       RTCGVCGDRATGFHFNAMTCEGCKGFFRRSMKRKALFTCPFN-GDCRITKDNRRHCQACR
VDR_x_laevis    RTCGVCGDRATGFHFNAMTCEGCKGFFRRSMKREAMFTCPFN-GDCRITKDNRRHCQSCR
VDR_zebrafish   RTCRVCGDKATGFHFNAMTCEGCKGFFRRSMKRKASFTCPFN-CRCRITKDNRRHCQACR
VDR_lamprey     KVCGVCGDRATGYHFNAMTCEGCKGFFRRSMKRSASFTCPFE-GKCRITKDNRRHCQACR
VDR_PXR_Clona   --------------MHFGAITCEGCKGFFRRSVKRNASFSCAF-ERKCEINKNNRRHCQACR
CAR_human       RMCVVCGDQATGYHFRALTCEGCKGFFRRTVSKSIGPTCPF-AGSCEVSKTQRRRCPACR PXR_human       LRRCLESGM (SEQ ID NO: 5)
PXR_chicken     LQKCLDVGM (SEQ ID NO: 6)
PXR_fugu        LRKCQAIGM (SEQ ID NO: 7)
VDR_human       LRKCVDIGM (SEQ ID NO: 8)
VDR_mouse       LRKCVDIGM (SEQ ID NO: 9)
VDR_x_laevis    LRKCVDIGM (SEQ ID NO: 10)
VDR_zebrafish   LRKCIDIGM (SEQ ID NO: 11)
VDR_lamprey     LKRCRDIGM (SEQ ID NO: 12)
VDR_PXR_Clona   FNACLAAGM (SEQ ID NO: 13)
CAR_human       LQKCIDAGM (SEQ ID NO: 14)
```

Figure 1B

B. Ligand-binding domain

Figure 2

(SEQ ID NO:1)

Meamaastslpdpgdfdrnvpricgvcgdratgfhfnamtcegckgffrrsmkrkalf tcpfngdcritkdnrrhcqacrlkrcvdigmmkefiltdeevqrkremilkrkeeealkD

SLRPKLSEEQQRIIAILLDAHHKTYDPTYSDFCQFRPPVRVN

D*GGGSHPSRPNSRHTPSFSGDSSSSCSDHCITSSDMMDSSS*

*FSNLDLSEEDSDDP*SVTLELSQLSMLPHLADLVSYSIQKVI

GFAKMIPGFRDLTSEDQIVLLKSSAIEVIMLRSNESFTMD

DMSWTCGNQDYKYRVSDVTKAGHSLELIEPLIKFQVGLK

KLNLHEEEHVLLMAICIVSPDRPGVQDAALIEAIQDRLSN

TLQTYIRCRHPPPGSHLLYAKMIQKLADLRSLNEEHSKQY

RCLSFQPECSMKLTPLVLEVFGNEIS

LBD

Figure 3

(SEQ ID NO:2)

MVSKGEELFTGVVPILVELDGDVNGHKFSVSGEGEGDATYGKLTLKLICTTGKLPVP
WPTLVTTLGYGVQCFARYPDHMKQHDFFKSAMPEGYVQERTIFFKDDGNYKTRAE
VKFEGDTLVNRIELKGIDFKEDGNILGHKLEYNYNSHNVYITADKQKNGIKANFKIR
HNIEDGGVQLADHYQQNTPIGDGPVLLPDNHYLSYQSKLSKDPNEKRDHMVLLEFV
TAAGITLGMDELYK

Figure 4

(SEQ ID NO:3)

MVSKGEELFTGVVPILVELDGDVNGHKFSVSGEGEGDATYGKLTLKFICTTGKLPVP
WPTLVTTLTWGVQCFARYPDHMKQHDFFKSAMPEGYVQERTIFFKDDGNYKTRAE
VKFEGDTLVNRIELKGIDFKEDGNILGHKLEYNYISDNVYITADKQKNGIKANFKIRH
NIEDGGVQLADHYQQNTPIGDGPVLLPDNHYLSTQSKLSKDPNEKRDHMVLLEFVT
AAGITLGMDELYK

Figure 5

(SEQ ID NO:4)

VSKGEELFTGVVPILVELDGDVNGHKFSVSGEGEGDATYGKLTLKLICTT
GKLPVPWPTLVTTLGYGVQCFARYPDHMKQHDFFKSAMPEGYVQERTI
FFKDDGNYKTRAEVKFEGDTLVNRIELKGIDFKEDGNILGHKLEYNYNSH
NVYITADKQKNGIKANFKIRHNIEDGGVQLADHYQQNTPIGDGPVLLPDN
HYLSYQSKLSKDPNEKRDHMVLLEFVTAAGITLGMDELYKDSLRPKLSEE
QQRIIAILLDAHHKTYDPTYSDFCQFRPPVRVNDGGSVTLELSQLSMLPHLA
DLVSYSIQKVIGFAKMIPGFRDLTSEDQIVLLKSSAIEVIMLRSNESFTMDDMS
WTCGNQDYKYRVSDYTKAGHSLELIEPLIKFQVGLKKLNLHEEEHVLLMAICI
VSPDRPGVQDAALIEAIQDRLSNTLQTYIRCRHPPPGSHLLYAKMIQKLADLR
SLNEEHSKQYRCLSFQPECSMKLTPLYLEVFGNEIS*GSGTGVSKGEELFTGVVP*
*ILVELDGDVNGHKFSVSGEGEGDATYGKLTLKFICTTGKLPVPWPTLVTTLT*
*WGVQCFARYPDHMKQHDFFKSAMPEGYVQERTIFFKDDGNYKTRAEVKFE*
*GDTLVNRIELKGIDFKEDGNILGHKLEYNYISDNVYITADKQKNGIKANFKIRH*
*NIEDGGVQLADHYQQNTPIGDGPVLLPDNHYLSTQSKLSKDPNEKRDHMVLL*
*EFVTAAGITLGMDELYK*

METHODS AND COMPOSITION FOR MEASURING THE AMOUNT OF VITAMIN D DERIVATIVES

BACKGROUND

1. Field of the Disclosure

The present invention relates generally to methods and compositions for measuring the amount of vitamin D derivatives. More particularly, the invention relates to the use of Fluorescence Resonance Energy Transfer (FRET) and a modified ligand-binding domain of the vitamin D receptor (LBD-VDR) to measure vitamin D derivatives.

2. Brief Description of Related Technology

Cholecalciferol and ergocalciferol (collectively are referred to as "Vitamin D") are fat-soluble seco-steroid precursors to Vitamin D prohormones. The Vitamin D metabolites known as 25-hydroxyvitamin $D_2$ and 25-hydroxyvitamin $D_3$ (collectively referred to herein as "25-hydroxyvitamin D") are fat-soluble steroid prohormones to Vitamin D hormones that contribute to the maintenance of normal levels of calcium and phosphorus in the bloodstream. Cholecalciferol and ergocalciferol are normally present at stable, low concentrations in human blood. Both cholecalciferol and ergocalciferol are metabolized into prohormones by enzymes primarily located in the liver of the human body. Cholecalciferol is metabolized into a prohormone 25-hydroxyvitamin $D_3$, and ergocalciferol is metabolized into two prohormones, 25-hydroxyvitamin $D_2$ and 24(S)-hydroxyvitamin $D_2$.

The Vitamin D prohormones are further metabolized in the kidneys into potent hormones. The prohormone 25-hydroxyvitamin $D_3$ is metabolized into a hormone $1\alpha,25$-dihydroxyvitamin $D_3$ (or calcitriol); likewise, 25-hydroxyvitamin $D_2$ and 24(S)-hydroxyvitamin $D_2$ are metabolized into hormones known as $1\alpha,25$-dihydroxyvitamin $D_2$ and $1\alpha,24(S)$-dihydroxyvitamin $D_2$, respectively. Production of these hormones from the prohormones also can occur outside of the kidney in cells which contain the required enzyme(s).

Surges in blood or intracellular prohormone concentrations can promote excessive extrarenal hormone production, leading to local adverse effects on calcium and phosphorus metabolism. Such surges also can inhibit hepatic prohormone production from subsequent supplemental Vitamin D and promote catabolism of both Vitamin D and 25-hydroxyvitamin D in the kidney and other tissues.

The Vitamin D hormones have essential roles in human health which are mediated by intracellular Vitamin D receptors (VDR). In particular, the Vitamin D hormones regulate blood calcium levels by controlling the absorption of dietary calcium by the small intestine and the reabsorption of calcium by the kidneys. Excessive hormone levels can lead to abnormally elevated urine calcium (hypercalciuria), blood calcium (hypercalcemia) and blood phosphorus (hyperphosphatemia). The Vitamin D hormones also participate in the regulation of cellular differentiation and growth, parathyroid hormone (PTH) secretion by the parathyroid glands, and normal bone formation and metabolism. Further, Vitamin D hormones are required for the normal functioning of the musculoskeletal, immune and renin-angiotensin systems. Numerous other roles for Vitamin D hormones are being postulated and elucidated based on the documented presence of intracellular VDR in nearly every human tissue.

The actions of Vitamin D hormones on specific tissues depend on the degree to which they bind to (or occupy) the intracellular VDR in those tissues. Cholecalciferol and ergocalciferol have affinities for the VDR which are estimated to be at least 100-fold lower than those of the Vitamin D hormones. As a consequence, physiological concentrations of cholecalciferol and ergocalciferol exert little, if any, biological actions without prior metabolism to Vitamin D hormones. However, supraphysiologic levels of cholecalciferol and ergocalciferol, in the range of 10 to 1,000 fold higher than normal, can sufficiently occupy the VDR and exert actions like the Vitamin D hormones. Similarly, the prohormones 25-hydroxyvitamin $D_2$ and 25-hydroxyvitamin $D_3$ have essentially identical affinities for the VDR which are also estimated to be at least 100-fold lower than those of the Vitamin D hormones. As a consequence, physiological concentrations of 25-hydroxyvitamin $D_2$ and 25-hydroxyvitamin $D_3$ have little, if any, biological actions without prior metabolism to Vitamin D hormones. However, supraphysiologic levels of 25-hydroxyvitamin $D_2$ and 25-hydroxyvitamin $D_3$, in the range of 10 to 1,000 fold higher than normal, can sufficiently occupy the VDR to exert actions like the Vitamin D hormones.

As with most nuclear receptors, VDR undergoes a conformational change upon ligand binding (helix 12 folds underneath H4; Rochel, N., et al,. *Mol. Cell.* 5, 173-179(2000); Nayeri, S and Carlberg, C. *Biochem J.* 327, 561-568 (1997)) The ligand binding domain of human VDR is comprised of amino acids~118-427. Amino acid residues involved in hydrogen bonding to the ligand include Ser-237, Arg-274, Tyr-143, Ser-278, His-305 and His-397. Amino acids that interact with the ligand through non-hydrogen bonding interactions include Tyr-147, Phe-150, Leu-227, Leu-230, Leu-233, Val-234, Ile-271, Ser-275, Trp-286, Cys-288, Val-300, Leu-309, Leu-313 and Val-418. Val-418 is located on the activation helix (helix 12) and is likely to undergo change in proximity as a result of ligand-induced conformational changes (Rochel, N., et al,. *Mol. Cell.* 5, 173-179(2000)).

One method that may be used to monitor protein-protein interactions is Fluorescence Resonance Energy Transfer (FRET) (Berrera et al., *Handb. Exp. Pharmacol.* 186, 285-298 (2008)). FRET microscopy detects energy transfer from a higher-energy donor fluorochrome to a lower-energy acceptor fluorochrome when they are close together. Resonance energy transfer is a mechanism by which energy is transferred directly from one molecule to another. This only occurs over a very small distance, usually less than 10 nm, which is on the order of the size of a typical protein. When each member of a protein-protein pair is labeled with appropriate fluorophores (donor and acceptor), FRET can be used to detect when the proteins are in proximity. It may also be possible to use FRET to detect conformational changes in a single protein tagged with two fluorophores.

SUMMARY 25-hydroxyvitamin D is the preferred vitamin D metabolite to measure when assessing vitamin D deficiency. 25-hydroxyvitamin D will drop before any effect would be seen at the calcitriol level. Thus, in patients where vitamin D levels are suspected to be abnormal (e.g., chronic kidney disease (CKD), bone disease, and the elderly), measuring and monitoring 25-hydroxyvitamin D levels is critical.

In one embodiment of the invention, a method for measuring the amount or concentration of a vitamin D derivative in a sample is provided comprising contacting a sample with a polypeptide comprising a modified VDR ligand-binding domain (VDR-LBD) and a donor-acceptor pair of fluorophores; and measuring the amount of fluorescence, wherein the amount of fluorescence is detectably higher or lower in the presence of the vitamin D derivative relative to the amount of fluorescence in the absence of the vitamin D derivative.

In another embodiment of the invention, the aforementioned method is provided wherein the vitamin D derivative is 25-hydroxyvitamin D. In still another embodiment, the modified VDR has at least a 5-fold, 10-fold, 15-fold, 20-fold, 30-fold, 40-fold, 50-fold, 60-fold, 70-fold, 80-fold, 90-fold, 100-fold, 200-fold, or 300-fold higher affinity for 25-hydroxyvitamin D than to other vitamin D derivatives. In a related embodiment, the modified VDR has at least a 10-fold higher affinity for 25-hydroxyvitamin D than to other vitamin D derivatives.

In still another embodiment of the invention, the aforementioned method is provided wherein the sample is from a mammalian or human subject. In another embodiment, the human is suffering from chronic kidney disease (CKD).

In yet another embodiment, the aforementioned method is provided wherein the modified VDR comprises at least one mutation causing said modified VDR to have a higher binding affinity to 25-hydroxyvitamin D relative to calcitriol. In another embodiment, the mutation comprises a substitution at an amino acid position such as, but not limited to, 274, 147, 150, 227, 230, 233, 234, 271, 275, 286, 288, 300, 309, 313, 418, 237, 143, 278, 305 and 397. In one embodiment, the mutation comprises a substitution at amino acid position 274. In a related embodiment, the mutation at position 274 comprises a substitution of a basic amino acid residue for an aliphatic amino acid residue. In still another embodiment, the mutation comprises Arg274Leu.

In another embodiment of the invention, the aforementioned method is provided wherein the fluorescence is measured using Fluorescence Resonance Energy Transfer (FRET). In another embodiment, the donor-acceptor pair of fluorophores is selected from the group consisting of green fluorescent protein (GFP), red fluorescent protein (RFP), cyan-fluorescent protein (CFP), yellow-fluorescent protein (YFP), and active fragments thereof.

Polypeptides are also provided in the instant invention. In one embodiment, a polypeptide is provided comprising a modified VDR ligand-binding domain (VDR-LBD) and a donor-acceptor pair of fluorophores, wherein said polypeptide comprises at least one mutation causing said modified VDR to have a higher binding affinity to 25-hydroxyvitamin D relative to calcitriol. In another embodiment, the aforementioned polypeptide is provided wherein the at least one mutation comprises a substitution at amino acid position such as, but not limited to, 274, 147, 150, 227, 230, 233, 234, 271, 275, 286, 288, 300, 309, 313, 418, 237, 143, 278, 305 and 397. In another embodiment, the mutation comprises a substitution at amino acid position 274. In a related embodiment, the mutation at position 274 comprises a substitution of a basic amino acid residue for an aliphatic amino acid residue. In still another embodiment, the mutation comprises Arg274Leu.

Further aspects and advantages will be apparent to those of ordinary skill in the art from a review of the following detailed description, taken in conjunction with the drawings. While the compositions and methods are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

FIGS. 1A and B shows an alignment of human VDR and homologs from other species, as well as the approximate location of DNA-binding domains, ligand-binding domains and helices for each sequence. Sequence alignment of (A) DNA-binding domain and (B) ligand-binding domain of three PXRs, five VDRs, Ciona intestinalis VDR/PXR, and human CAR. The ligand-binding domain is annotated with the α-helices [1]. Accession numbers are: human PXR [Genbank:AF061056], chicken PXR [Genbank:AF276753], takifugu PXR [Ensembl,http://www.ensembl.org:NEWSINFRUT00000171584], human VDR [Genbank:NM_00376], mouse VDR [Genbank:NM_008504], Xenopus laevis VDR [Genbank:U91849], zebrafish VDR [Genbank:AF164512], sea lamprey VDR [Genbank:AY249863], Ciona intestinalis VDR/PXR [Genbank:BR000137], and human CAR [Genbank:NM_005122]. Moore et al., Mol. Endocrinol., 16:977-986 (2002).

FIG. 2 shows a human VDR amino acid sequence (SEQ ID NO: 1) and localization of Ser-237 and Arg-274 as indicated in bold. The amino acids of the ligand binding domain (LBD) are indicated by capital letters. The amino acids that in some embodiments may not be expressed are indicated by italics. Removal of this relatively unconserved and flexible sequence allows for crystallization and does not have any effect on ligand binding, dimerization with RXR, or transactivation in vitro (Rochel, 2000).

FIG. 3 shows the yellow fluorescent protein (YFP) amino acid sequence (SEQ ID NO: 2).

FIG. 4 shows the cyan fluorescent protein (CFP) amino acid sequence (SEQ ID NO: 3).

FIG. 5 shows one example of a VDR-LBDm amino acid sequence (SEQ ID NO: 4) (sYFP2-VDRLBDdelta-linker-sCFP3A).

DETAILED DESCRIPTION

Figure 6:
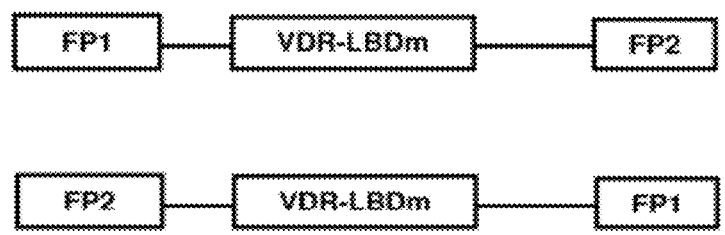
FIG. 6 shows two possible constructs of modified VDR-LBD (VDR-LBDm)

The present invention discloses a rapid and clinically accessible assay for the measurement of vitamin D molecules. For this purpose, highly sensitive biosensors are constructed based on the ligand-binding domain of the VDR (VDR-LBD). Upon the binding of ligand (eg., vitamin D or an active vitamin D analog), or upon release of a bound ligand, the LBD undergoes a conformational change. These events can be monitored by adapting paired donor-acceptor flourophores to the VDR-LBD whose proximity to each other are altered as a result of the ligand-induced change in conformation. This change in proximity can generate a measurable signal through Fluorescent Resonance Energy Transfer (FRET), which is the transfer of energy from a donor fluorophore to an acceptor. In one embodiment, FRET will occur between the reporter proteins SCFP3A and SYFP2 that are adapted to the VDR-LBD. By way of example, in one embodiment the reporter proteins are SCFP3A (SCFP3A accession number: AAZ65848) Kremers, G.-J., et al (2006) Biochemistry 45, 6570-6580) and SYFP2 (SYFP2 accession number: AAZ65845) Kremers, G.-J., et al (2006) Biochemistry 45, 6570-6580).

Unless otherwise defined, all technical and scientific terms used herein have the same meaning as commonly understood by one of ordinary skill in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that, as used in this specification and the appended claims, the singular forms "a," "an," and "the" include plural reference unless the context clearly dictates otherwise.

The term "subject" as used herein generally includes humans, mammals (e.g., dogs, cats, rodents, sheep, horses, cows, goats), veterinary animals and zoo animals.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range or a beneficial effect range is stated as 1% to 50%, it is intended that values such as 2% to 40%, 10% to 30%, or 1% to 3%, etc., are expressly enumerated in this specification. These are only examples of what is specifically intended.

The term "comprising," with respect to a peptide compound, means that a compound may include additional amino acids and/or other chemical moieties at either or both amino- and carboxy-termini of the given sequence. Of course, these additional amino acids or other chemical moieties should not significantly interfere with the activity of the compound. With respect to a composition of the instant invention, the term "comprising" means that a composition may include additional components. These additional components should not significantly interfere with the activity of the composition.

As used herein the terms "express," "expressing" and "expression" mean allowing or causing the information in a gene or DNA sequence to become manifest, for example, producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed." An expression product can be characterized as intracellular, extracellular or secreted.

As used herein a "polypeptide" refers to a polymer composed of amino acid residues, structural variants, related naturally-occurring structural variants, and synthetic non-naturally occurring analogs thereof linked via peptide bonds. Synthetic polypeptides can be prepared, for example, using an automated polypeptide synthesizer. The term "protein" typically refers to large polypeptides. The term "peptide" typically refers to short polypeptides.

As used herein a "fragment" of a polypeptide is meant to refer to any portion of a polypeptide or protein smaller than the full-length polypeptide or protein expression product.

As used herein an "analog" refers to a modified polypeptide substantially similar in structure to the parent polypeptide. The modified polypeptide may have a similar or altered biological activity, or varying degrees of activity, compared to either the entire parent molecule, or to a fragment thereof. For example, the modified polypeptide may have similar or altered (increased or decreased) binding affinity for a ligand or receptor of the parent polypeptide. Analogs differ in the composition of their amino acid sequences based on one or more mutations. Amino acid sequence analogs of a polypeptide can be substitutional, insertional, addition or deletion analogs. Deletion analogs, including fragments of a polypeptide, lack one or more residues of the native protein which are not essential for function or immunogenic activity. Insertional analogs involve the addition of, e.g., amino acid(s) at a non-terminal point in the polypeptide. This analog may include insertion of an immunoreactive epitope or simply a single residue. Addition analogs, including fragments of a polypeptide, include the addition of one or more amino acids at either of both termini of a protein and include, for example, fusion proteins. Substitutions can be conservative or non-conservative based on the physico-chemical or functional relatedness of the amino acid that is being replaced and the amino acid replacing it.

As used herein, a "conservative substitution" of an amino acid is a substitution of one amino acid with another amino acid that has similar physical and chemical properties, e.g. in terms of size, volume, charge, hydrophobicity, hydrophilicity, and the like. Amino acids may be grouped by similarities, e.g. properties like hydrophobic, hydrophilic, acidic, basic, polar, apolar, aromatic, small aliphatic, large aliphatic, etc. Similar amino acids for making conservative substitutions include those having an acidic side chain (glutamic acid, aspartic acid); a basic side chain (arginine, lysine, histidine); a polar amide side chain (glutamine, asparagine); a hydrophobic, aliphatic side chain (leucine, isoleucine, valine, alanine, glycine); an aromatic side chain (phenylalanine, tryptophan, tyrosine); a small side chain (glycine, alanine, serine, threonine, methionine); or an aliphatic hydroxyl side chain (serine, threonine). The conservative nature of a substitution may depend on the location of the amino acid within a polypeptide sequence.

As used herein a "variant" refers to a polypeptide, protein or analog thereof that is modified to comprise additional chemical moieties not normally a part of the molecule. Such moieties may modulate the molecule's solubility, absorption, biological half-life, etc. The moieties may alternatively decrease the toxicity of the molecule and eliminate or attenuate any undesirable side effect of the molecule, etc. Moieties capable of mediating such effects are disclosed in Remington's Pharmaceutical Sciences (1980). Procedure for coupling such moieties to a molecule are well known in the art.

As used herein, a "recombinant polynucleotide" or "recombinant nucleic acid" refers to a polynucleotide having sequences that are not naturally joined together. For example, a nucleic acid coding for a polypeptide may be joined with a heterologous regulatory control sequence or other non-coding sequence (e.g., promoter, operator, origin of replication, ribosome binding site, etc.). Two or more polynucleotides joined in such a manner may be included together in a vector, and the vector can be used to transform a suitable host cell. A host cell that comprises the recombinant polynucleotide is referred to as a "recombinant host cell." Alternatively, a host cell in which a polynucleotide is naturally present may be modified by addition of a heterologous regulatory control sequence that controls expression of the host cell's natural occurring polynucleotide. Such a host cell is also referred to as a "recombinant host cell." The expression product produced by a recombinant host cell is referred to as a "recombinant polypeptide."

As used herein "biologically active derivative" or "biologically active variant" includes any derivative or variant of a molecule having substantially the same functional and/or biological properties of said molecule, such as binding properties, and/or the same structural basis, such as a peptidic backbone or a basic polymeric unit.

Recombinant Vitamin D Receptor

As used herein, the term "vitamin D derivatives" refers to metabolites or derivatives of cholecalciferol and ergocalciferol (collectively referred to as "Vitamin D"), and includes but is not limited to the Vitamin D metabolites 25-hydroxyvitamin $D_2$ and 25-hydroxyvitamin $D_3$ (collectively referred to herein as "25-hydroxyvitamin D"); 1α,25-dihydroxyvitamin $D_3$ (or calcitriol); 24(S)-hydroxyvitamin $D_2$; 1α,25-dihydroxyvitamin $D_2$; and 1α,24(S)-dihydroxyvitamin $D_2$ The compounds 1α,25-dihydroxyvitamin $D_3$ (or calcitriol) and 1α,25-dihydroxyvitamin $D_2$ are collectively referred to herein as "1, 25-hydroxyvitamin D". The term vitamin D derivatives also embraces vitamin D analogs such as Paricalcitol, or any modified vitamin D molecules such as variants, etc, as described herein.

The term "vitamin D receptor" (VDR) includes naturally occurring, recombinant or synthetic vitamin D receptor, as well as polymorphic variants, alleles, naturally-occurring mutants, and species homologs thereof. The VDR is a member of a superfamily of nuclear steroid hormone receptors which regulate gene transcription by interacting with response elements in gene promoters. Structure-function analysis of the VDR protein has defined distinct domains involved in DNA binding, ligand binding, receptor dimerization and gene transactivation, including a C-terminal activation function domain (AF-2) that is important for cofactor interaction (Issa, L. L., et al., Inflamm. Res., 47(12):451-475 (1998)). As with most nuclear receptors, VDR undergoes a conformational change upon ligand binding; helix 12 folds underneath Helix 4 (Rochel, N., et al., *Mol. Cell.* 5, 173-179) (2000)). The active form of vitamin D (1α,25-dihydroxyvitamin $D_3$; 1α,25-dihydroxyvitamin $D_2$; and 1α,24(S)-dihydroxyvitamin $D_2$) binds to intracellular receptors such as the vitamin D receptor that then function as transcription factors to modulate gene expression Like the receptors for other steroid hormones and thyroid hormones, the vitamin D receptor has hormone-binding and DNA-binding domains. The vitamin D receptor forms a complex with another intracellular receptor, the retinoid-X receptor, and that heterodimer is what binds to DNA.

A sequence of human VDR (SEQ ID NO: 1), 427 amino acids in length, is displayed in FIG. 2. Amino acids 118-427 correspond to the vitamin D-binding domain (the ligand binding domain, or "VDR-LBD"). Amino acids~20-112 correspond to the DNA-binding domain. FIGS. 1A and B displays an alignment of human VDR and homologs from other species, as well as the approximate location of DNA-binding domains, ligand-binding domains and helices for each sequence (Reschly et al., BMC Evolutionary Biology, 7:222 (2007)). Helix 12 corresponds to amino acids~417-422. Helix 4 corresponds to amino acids~256-267.

One of ordinary skill in the art can determine, e.g. from FIGS. 1A and B, amino acids and regions that are highly conserved among species (i.e., the amino acids are identical or a conservative substitution with an amino acid of similar properties). Identification of these regions provide guidance in modifying the VDR to prepare analogs or variants. For example, conservative substitutions, or modifications outside of the highly conserved regions, are generally expected to lead to either no change or only a small change in the properties of the VDR, e.g., vitamin D derivative binding activity, transcription factor activity, and/or retinoid-X receptor binding activity. Thus, in preparing analogs and variants that retain substantially the same properties as VDR, one of ordinary skill in the art would begin by making conservative or non-conservative substitutions in regions that are not highly conserved, while retaining the same amino acids or making conservative substitutions within highly conserved regions. Similarly, in preparing analogs and variants with altered properties compared to VDR, one of ordinary skill in the art would begin by making non-conservative substitutions in the domain(s) associated with the property to be altered. By way of example, Tyr-147, Phe-150, Leu-227, Leu-230, Leu-233, Val-234, Ile-271, Ser-275, Trp-286, Cys-288, Val-300, Leu-309, Leu-313 and Val-418. Val-418, Ser-237, Arg-274, Tyr-143, Ser-278, His-305 and His-397 could be modified to generate new properties for VDR.

The invention provides fragments of VDR that comprise the ligand binding domain (VDR-LBD), or analogs or variants thereof, and uses thereof in the detection methods of the invention. As used herein, the term "modified VDR-LBD" refers to LBD fragments of VDR or analogs or variants thereof that exhibit altered (increased or decreased) binding affinity for one vitamin D derivative relative to a different vitamin D derivative, and uses thereof in the detection methods of the invention. For example, typically VDR exhibits a greater binding affinity for 1, 25-hydroxyvitamin D relative to 25-hydroxyvitamin D. According to one embodiment of the invention, a modified VDR-LBD that favors 25-hydroxyvitamin D binding over that for calcitriol, is provided. Such a modified VDR-LBD (e.g., VDR-LBDm), can be used according to the methods of the invention to detect the presence of 25-hydroxyvitamin D. In some embodiments, the modified VDR-LBD has at least an approximately 10-fold, 25-fold, 50-fold, 75-fold, 100-fold, 200-fold, 300-fold, 400-fold, 500-fold or greater binding affinity for 25-hydroxyvitamin D compared to 1, 25-hydroxyvitamin D. In some embodiments, modified VDR-LBD has a greater binding affinity for 25-hydroxyvitamin $D_2$ compared to 1, 25-hydroxyvitamin $D_2$, while in other embodiments, the modified VDR-LBD has a greater binding affinity for 25-hydroxyvitamin $D_3$ compared to 1, 25-hydroxyvitamin $D_3$.

The C1 hydroxyl group of calcitriol is coordinated in the VDR-LBD binding pocket by forming hydrogen bonds with Ser-237 and Arg-274. Presumably, this stabilizes calcitriol binding over that of 25-hydroxyvitamin D. It is known that a natural mutation at Arg-274 (Arg274Leu) results in vitamin D—resistant rickets. The binding affinity of a VDR with this particular mutation is approximately 1000-fold lower than that for the wild-type VDR (Kristjansson, K., Rut, A. R., Hewison, M., O'Riordan J. L. & Hughes, M. R. *Two mutations in the hormone binding domain of the vitamin D receptor cause tissue resistance to 1,25 dihydroxyvitamin D3* (1993) *J. Clin. Invest.,* 92, 12-16. Since the bulky hydrophobic side chain of leucine at Arg274Leu would interfere with the C1-hydroxyl group positioning, such a mutation will favor 25-hydroxyvitamin D binding. Mutations have been introduced at Ser-237, including a Ser237Ala mutant which shows approximately 27-fold weaker binding for 1,25-hydroxyvitamin $D_3$, due to the loss of a stabilizing hydrogen bond (Yamada, S, Yamamoto, K., Masuno, H. & Choi, M. *Three-dimensional structure function relationship of vitamin D and vitamin D receptor model.* (2001) *Steroids* 66, 177-187.). It can be envisioned that mutation of Ser-237 to a more bulky hydrophobic side chain will result both in a loss of a stabilizing hydrogen bond and increased steric conflicts with the 1-hydroxyl group, thereby favoring binding of 25-hydroxyvitamin D over 1-25-dihydroxyvitamin D. Also, synthetic VDR-LBDs can be constructed which modify either or both of Ser-237 and Arg-274 with various amino acid side chain groups that will interfere with calcitriol binding but favor that of 25-hydroxyvitamin D. Examples of such mutations include, but are not limited to, Ser237Val, Ser237Ile, Ser237Leu, Ser237Ala, Arg274Leu, Arg274Val and Arg274Ile. A number of VDR-LBD constructs can be contemplated which may favour 25-dihydroxyvitamin D binding over that of calcitriol and thus could be used in the FRET based construct for analyzing the presence of 25-dihydroxyvitamin D.

Modified VDR-LBD provided by the invention include, for example and without limitation, polypeptides comprising the ligand binding domains described hereinabove or analogs or variants thereof, polypeptides encoded by a nucleic acid described herein, and/or polypeptides comprising an amino acid sequence that has greater than about 60%, about 65%, about 70%, about 75%, about 80%, about 85%, about 90%, about 91%, about 92%, about 93%, about 94%, about 95%, about 96%, about 97%, about 98% or about 99% or greater amino acid sequence identity to, over a region of at least about 25, about 50, about 100, about 200, about 300, about 400, or more amino acids of, the ligand binding domain of the native protein, including conservative or non-conservative substitutions thereto. In some embodiments, a modified VDR-LBD comprises an amino acid sequence that is specifically bound by an antibody, e.g., polyclonal or monoclonal antibodies, generated against any of the ligand binding domains described herein. Such modified VDR-LBD will retain the binding affinity for vitamin D derivative that is exhibited by SEQ ID NO: 1, or a species homolog thereof. Alternatively, such modified VDR-LBD will exhibit an altered binding affinity for vitamin D derivatives as described herein, including but not limited to a relatively higher binding affinity for 25-hydroxyvitamin D compared to 1, 25-hydroxyvitamin D. In some embodiments, such a modified VDR-LBD with relatively higher binding affinity for 25-hydroxyvitamin D may comprise an amino acid mutation (insertion, deletion, or substitution) at any one or more of position 237, 274 . . . of SEQ ID NO: 1. In some embodiments, the mutation at position 274 comprises a substitution of a basic amino acid residue for an aliphatic amino acid residue. In some embodiments, the mutation is a Arg274Leu substitution. In some embodiments, the modified VDR-LBD will delete certain amino acid sequences including sequences considered to be structurally variable e.g. amino acids 165-215 may be deleted to yield a ligand binding domain consisting of amino acids 118-164 followed directly by amino acids 216-427.

Polynucleotides encoding a modified VDR-LBD of the invention include, without limitation, those that (1) specifically hybridize under stringent hybridization conditions to a nucleic acid encoding a referenced amino acid sequence as described herein, and conservatively modified variants thereof; (2) have a nucleic acid sequence that has greater than about 95%, about 96%, about 97%, about 98%, about 99%, or higher nucleotide sequence identity, over a region of at least about 25, about 50, about 100, about 150, about 200, about 250, about 500, about 1000, or more nucleotides (up to the full length sequence of 1281 nucleotides of the mature protein), to a reference nucleic acid sequence as described herein.

Polynucleotides encoding fragments, variants and analogs may be readily generated by a worker of skill to encode biologically active fragments, variants, or analogs of the naturally-occurring molecule that possess the same or similar biological activity to the naturally-occurring molecule. These polynucleotides can be prepared using PCR techniques, digestion/ligation of DNA encoding molecule, and the like. Thus, one of skill in the art will be able to generate single base changes in the DNA strand to result in an altered codon and a missense mutation, using any method known in the art, including, but not limited to site-specific mutagenesis. As used herein, the phrase "moderately stringent hybridization conditions" means, for example, hybridization at 42° C. in 50% formamide and washing at 60° C. in 0.1×SSC, 0.1% SDS. It is understood by those of skill in the art that variation in these conditions occurs based on the length and GC nucleotide base content of the sequences to be hybridized. Formulas standard in the art are appropriate for determining exact hybridization conditions. See Sambrook et al., 9.47-9.51 in Molecular Cloning, Cold Spring Harbor Laboratory Press, Cold Spring Harbor, N.Y. (1989).

Analogs may be substantially homologous or substantially identical to the recombinant VDR or VDR-LBD from which they are derived.

Substitutional analogs typically exchange one amino acid of the wild-type for another at one or more sites within the protein, and may be designed to modulate one or more properties of the polypeptide without the loss of other functions or properties. In one aspect, substitutions are conservative substitutions. It is further contemplated that a polypeptide of the invention may be a fusion protein with a second agent which is a polypeptide. In one embodiment, the second agent which is a polypeptide, without limitation, is a fluorophore useful in FRET, an enzyme, a growth factor, an antibody, a cytokine, a chemokine, a cell-surface receptor, the extracellular domain of a cell surface receptor, a cell adhesion molecule, a purification tag, a ligand-binding protein, or fragment or active domain of a protein described above. The two polypeptides comprising the fusion protein may be separated by a third polypeptide segment known as a linker, which may consist of any number of amino acids greater than or equal to one. The fusion protein contemplated is made by chemical or recombinant techniques well-known in the art.

Cloning, Expression And Purification Of Vitamin D Receptor

The recombinant vitamin D receptor of the present invention may be produced by any method known in the art. Thus, methods are known in the art for (i) the production of recombinant DNA by genetic engineering, e.g. via reverse transcription of RNA and/or amplification of DNA, (ii) introducing recombinant DNA into procaryotic or eucaryotic cells by transfection, e.g. via electroporation, transformation or microinjection, (iii) cultivating said transformed cells, e.g. in a continuous or batchwise manner, (iv) expressing recombinant vitamin D receptor, e.g. constitutively or upon induction, and (v) isolating said recombinant vitamin D receptor, e.g. from the culture medium or by harvesting the transformed cells, in order to (vi) obtain purified recombinant vitamin D receptor, e.g. via anion exchange chromatography or affinity chromatography. A recombinant vitamin D receptor may be made in transformed host cells using recombinant DNA techniques well known in the art. For instance, sequences coding for the polypeptide could be excised from DNA using suitable restriction enzymes.

Alternatively, the DNA molecule could be synthesized using chemical synthesis techniques, such as the phosphoramidate method. Also, a combination of these techniques could be used. The polypeptides of the invention may be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides.

Methods for preparing polypeptide fragments, variants or analogs are well-known in the art.

Fragments of a polypeptide are prepared using, without limitation, enzymatic cleavage (e.g., trypsin, chymotrypsin) and also using recombinant means to generate a polypeptide fragments having a specific amino acid sequence. Polypeptide fragments may be generated comprising a region of the protein having a particular activity, such as a ligand-binding domain or any other identifiable VDR domain known in the art.

Methods of making polypeptide analogs are also well-known. The invention also provides vectors encoding polypeptides of the invention in an appropriate host. The vector comprises the polynucleotide that encodes the polypeptide operatively linked to appropriate expression control sequences. Methods of effecting this operative linking, either before or after the polynucleotide is inserted into the vector, are well known. Expression control sequences include promoters, activators, enhancers, operators, ribosomal binding sites, start signals, stop signals, cap signals, polyadenylation signals, and other signals involved with the control of transcription or translation. The resulting vector having the polynucleotide therein is used to transform an appropriate host. This transformation may be performed using methods well known in the art.

In still other aspects, a wide variety of vectors are used for the preparation of the VDR or VDR-LBD and are selected from eukaryotic and prokaryotic expression vectors. Examples of vectors for prokaryotic expression include plasmids such as, and without limitation, pRSET, pET, and pBAD, wherein the promoters used in prokaryotic expression vectors include one or more of, and without limitation, lac, trc, trp, recA, or araBAD. Examples of vectors for eukaryotic expression include: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as and without limitation pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and β-actin.

Any of a large number of available and well-known host cells may be used in the practice of this invention. The selection of a particular host is dependent upon a number of factors recognized by the art, including, for example, compatibility with the chosen expression vector, toxicity of the peptides encoded by the DNA molecule, rate of transformation, ease of recovery of the peptides, expression characteristics, biosafety and costs. A balance of these factors must be struck with the understanding that not all host cells are equally effective for the expression of a particular DNA sequence. Within these general guidelines, useful microbial host cells include bacteria, yeast and other fungi, insects, plants, mammalian (including human) cells in culture, or other hosts known in the art. Examples of eukaryotic cells are mammalian cells, such as CHO, COS, HEK 293, BHK, SK-Hep, and HepG2.

Next, the transformed host is cultured and purified. Host cells may be cultured under conventional fermentation conditions so that the desired compounds are expressed. Such fermentation conditions are well known in the art. Finally, the polypeptides are isolated and optionally purified from culture, either culture media or the host cells, by methods well known in the art.

Methods of Detecting

The methods of the invention monitor the conformational changes induced by binding of the vitamin D derivative to the VDR, polypeptide comprising a modified VDR-LBD. The binding of vitamin D derivative results in detectable conformational changes that quantitatively correspond to the amount of vitamin D derivative present in a sample. A variety of samples can be analyzed according to the methods of the present invention, including analytical samples, bulk drug product, finished or filled drug product, or patient and animal samples, such as blood, plasma, serum, urine, saliva, and tissue.

Numerous methods are available to monitor the conformational changes induced by protein-protein interactions (e. g., ligand-receptor binding) (Protein-Ligand Interactions: Methods and Applications. (2005) Methods in Molecular Biology, Vol 305. G. Ulrich Nienhaus, Editor) see also (Protein-Protein Interactions: Methods and Applications. (2004) Methods in Molecular Biology, Vol 261. Haian Fu, Editor)). These techniques can be adapted to the methods of the present invention. One example of a suitable technique is Fluorescence Resonance Energy Transfer, or FRET, which detects the non-radiative transfer of photon energy from an excited fluorophore (the donor) to another fluorophore (the acceptor) when both are located within close proximity (e.g., 1-10 nm). FRET is thus capable of resolving the relative proximity of a pair of molecules beyond the optical limit of a light microscope. Conventional application of FRET technology has been to monitor molecular interactions between two protein partners, e.g., when each member of a protein-protein pair is labeled with appropriate donor and acceptor fluorophores. In some circumstances, it is possible to monitor structural changes within a single molecule tagged with two fluorophores. (De, S., Macara, I. G. & Lannigan, D. A. *Novel biosensors for the detection of estrogen receptor ligands.* (2005) *J. Ster. Biochem. Mol. Biol.* 96, 235-244.)

In FRET imaging, typically the emission spectrum of the donor overlaps the absorption spectrum of the acceptor, such that energy transfer occurs when the donor and acceptor molecules are in close proximity (typically 10-100 Å, which is 1-10 nm). For comparison the diameter of a DNA double helix is 2.3 nm, an F-actin filament ~6 nm, an intermediate filament ~10 nm, and a microtubule 25 nm). Optimal energy transfer occurs when the donor and acceptor transition dipole orientations are approximately parallel. FRET imaging can be performed with number of microscopy techniques known in the art, including but not limited to widefield fluorescence microscopy or confocal microscopy.

Thus, the VDR, or polypeptide comprising a modified VDR-LBD, optionally comprises at least two, three, or more fluorophores, preferably a donor-acceptor pair of fluorophores, selected so that the polypeptide exhibits increased or decreased fluorescence in the presence of vitamin D derivative relative to the amount of fluorescence in the absence of vitamin D derivative.

As used herein, "fluorophore" means a compound that comprises a functional group that will absorb energy of a specific wavelength and re-emit energy at a different (but equally specific) wavelength. The fluorophore's properties depend on the compound's absorption and emission spectra, quantum efficiency (the ratio between the energy absorbed and the energy emitted), and the chemical environment of the fluorophore.

As used herein, a "donor-acceptor pair of fluorophores" is a set of at least two fluorophores (donor and acceptor) selected to be capable of producing detectable energy transfer when brought in proximity to each other, e.g. 1-10 nm.

Fluorophores include Fluorescent proteins (FPs) like the green-fluorescent-protein (GFP) from *Aequoria victoria*, red fluorescent protein (RFP), analogs, variants and homologs thereof. They can be genetically fused to proteins of interest and expressed in cells making them an excellent reporter system for gene expression and protein localization in living cells. Several enhanced FP variants with different spectral and biochemical properties are available. FPs that emits in the cyan region can be optimally paired for FRET with FPs that emits in the yellow region since the emission spectrum of CFPs partially overlaps the excitation spectrum of YFP. When CFPs is excited at approximately 430 nm, YFP emits at 545 nm if the two proteins are within close proximity. When these fluorophores are separated, there is a measurable and corresponding drop in FRET. Fluorescent proteins include but are not limited to Y66H, Y66F, EBFP, EBFP2, SYPF2, SCFP3A, Azurite, GFPuv, T-Sapphire, Cerulean, mCFP, ECFP, CyPet, Y66W, mKeima-Red, TagCFP, AmCyan1, mTFP1, S65A, Midoriishi Cyan, Wild Type GFP, S65C, TurboGFP, TagGFP, S65L, Emerald, S65T, EGFP, Azami Green, ZsGreen1, TagYFP, EYFP, Topaz, Venus, mCitrine, YPet, TurboYFP, ZsYellow1, Kusabira Orange, mOrange, mKO, TurboRFP, tdTomato, TagRFP, DsRed monomer, DsRed2 ("RFP"), mStrawberry, TurboFP602, AsRed2, mRFP1, J-Red, mCherry, HcRed1, Katusha, mKate (TagFP635), TurboFP635, mPlum, and/or mRaspberry (Shaner, N. C., Patterson, G. H. & Davidson, M. W. *Advances in fluorescent protein technology* (2007) *J. Cell. Sci.* 120, 4247-4260)).

Other fluorophores include but are not limited to Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, TRITC, X-Rhodamine, Lissamine Rhodamine B, Texas Red, Allophycocyanin (APC), APC-Cy7 conjugates, Alexa Fluor dyes, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, Alexa Fluor 790, Cy Dyes (GE Heathcare), Cy2, Cy3, Cy3B, Cy3.5, Cy5, Cy5.5, Cy7, Nucleic acid probes, Hoechst 33342, DAPI, Hoechst 33258, SYTOX Blue, Chromomycin A3, Mithramycin, YOYO-1, Ethidium Bromide, Acridine Orange, SYTOX Green, TOTO-1, TO-PRO-1, Thiazole Orange, Propidium Iodide (PI), LDS 751, 7-AAD, SYTOX Orange, TOTO-3, TO-PRO-3, DRAQ5, Indo-1, Fluo-3, DCFH, DHR, SNARF, Monochlorobimane, Calcein, time resolved fluorescence reagents including lanthanide (Sm, Eu, Tb, Dy) chelates and cryptates such as Europium cryptate, Lumi4-Tb, XL665, d2.

In some embodiments, the donor-acceptor pair of fluorophores is SCFP3A and SYFP2

In some embodiments of the invention, the methods are capable of detecting concentrations of vitamin D derivative ranging from about 1 to about 100 ng/ml, 0.1 to about 1000 ng/ml, 0.5 to about 100 ng/ml, 1 to about 50 ng/ml, 25 to about 75 ng/ml, or broader ranges. Physiological concentration of 25-hydroxyvitamin D is about 25.0 to 80.0 nanograms per milliliter (ng/mL), and 1,25-dihydroxyvitamin D is about 22.0 to 67.0 picograms per milliliter (pg/mL).

It is understood that any numerical value recited herein includes all values from the lower value to the upper value, i.e., all possible combinations of numerical values between the lowest value and the highest value enumerated are to be considered to be expressly stated in this application. For example, if a concentration range or a beneficial effect range is stated as 1 to 50, it is intended that values such as 2 to 40, 10 to 30, or 1 to 3, etc., are expressly enumerated in this specification. These are only examples of what is specifically intended.

The compositions, methods and kits of the invention are useful for evaluating body fluid or body tissue samples, e.g., blood, plasma, serum, CSF, urine or tissue samples, from any subject. Suitable subjects include healthy subjects, subjects in need of vitamin D supplementation, subjects at risk of insufficiency or deficiency of vitamin D or vitamin D derivatives, subjects suffering from insufficiency or deficiency of vitamin D or vitamin D derivatives, subjects being treated with vitamin D or vitamin D derivatives, and subjects with vitamin D-responsive diseases.

In some embodiments, the methods of the invention are applied to detect vitamin D derivative in samples from patients in need of vitamin D supplementation, including but not limited to healthy subjects and subjects at risk for vitamin D insufficiency or deficiency, for example, subjects with stage 1, 2, 3, 4 or 5 chronic kidney disease (CKD); subjects with renal osteodystrophy (including osteomalacia and osteitis fibrosa cystica); infants, children and adults that do not drink vitamin D fortified milk (e.g. lactose intolerant subjects, subjects with milk allergy, vegetarians who do not consume milk, and breast fed infants); subjects with rickets; subjects with dark skin (e.g., in the U.S., 42% of African American women between 15 and 49 years of age were vitamin D deficient compared to 4% of white women); the elderly (who have a reduced ability to synthesize vitamin D in skin during exposure to sunlight and also are more likely to stay indoors); institutionalized adults (who are likely to stay indoors, including subjects with Alzheimer's disease or mentally ill); subjects who cover all exposed skin (such as members of certain religions or cultures); subjects who always use sunscreen (e.g., the application of sunscreen with an Sun Protection Factor (SPF) of 8 reduces production of vitamin D by 95%, and higher SPFs may further reduce cutaneous vitamin D production); subjects with fat malabsorption syndromes (including but not limited to cystic fibrosis, cholestatic liver disease, other liver disease, gallbladder disease, pancreatic enzyme deficiency, Crohn's disease, inflammatory bowel disease, sprue or celiac disease, or surgical removal of part or all of the stomach and/or intestines); subjects with inflammatory bowel disease; subjects with Crohn's disease; subjects who have had small bowel resections; subjects with gum disease; subjects taking medications that increase the catabolism of vitamin D, including phenytoin, fosphenytoin, phenobarbital, carbamazepine, and rifampin; subjects taking medications that reduce absorption of vitamin D, including cholestyramine, colestipol, orlistat, mineral oil, and fat substitutes; subjects taking medications that inhibit activation of vitamin D, including ketoconazole; subjects taking medications that decrease calcium absorption, including corticosteroids; subjects with obesity (vitamin D deposited in body fat stores is less bioavailable); subjects with osteoporosis and/or postmenopausal women.

In some embodiments, the methods of the invention are applied to detect vitamin D derivative in samples from patients with vitamin D-responsive diseases, i.e., diseases where vitamin D, 25(OH)D or active vitamin D (e.g., 1, 25(OH)$_2$D) prevents onset or progression of disease, or reduces signs or symptoms of disease. Such vitamin D-responsive diseases include cancer (e.g., breast, lung, skin, melanoma, colon, colorectal, rectal, prostate and bone cancer). 1,25(OH)$_2$D has been observed to induce cell differentiation and/or inhibit cell proliferation in vitro for a number of cells. Vitamin D-responsive diseases also include autoimmune diseases, for example, type I diabetes, multiple sclerosis, rheumatoid arthritis, polymyositis, dermatomyositis, scleroderma, fibrosis, Grave's disease, Hashimoto's disease, acute or chronic transplant rejection, acute or chronic graft versus host disease, inflammatory bowel disease, Crohn's disease, systemic lupus erythematosis, Sjogren's Syndrome, eczema and psoriasis, dermatitis, including atopic dermatitis, contact dermatitis, allergic dermatitis and/or chronic dermatitis. Vitamin D-responsive diseases also include other inflammatory diseases, for example, asthma, chronic obstructive pulmonary disease, polycystic kidney disease (PKD), polycystic ovary syndrome, pancreatitis, nephritis, hepatitis, and/or infection. Vitamin D-responsive diseases have also been reported to include hypertension and cardiovascular diseases. Thus, the methods of the invention include testing samples from subjects at risk of or suffering from cardiovascular diseases, for example, subjects with atherosclerosis, arteriosclerosis, coronary artery disease, cerebrovascular disease, peripheral vascular disease, myocardial infarction, myocardial ischemia, cerebral ischemia, stroke, congestive heart failure, cardiomyopathy, obesity or other weight disorders, lipid disorders (e.g. hyperlipidemia, dyslipidemia including associated diabetic dyslipidemia and mixed dyslipidemia hypoalphalipoproteinemia, hypertriglyceridemia, hypercholesterolemia, and low HDL (high density lipoprotein)), metabolic disorders (e.g. Metabolic Syndrome, Type II diabetes mellitus, Type I diabetes mellitus, hyperinsulinemia, impaired glucose tolerance, insulin resistance, diabetic complication including neuropathy, nephropathy, retinopathy, diabetic foot ulcer and cataracts), and/or thrombosis.

EXAMPLES

The following Examples are provided for illustration and are not intended to limit the scope of the invention.

Example 1

Vitamin D Biosensor

A modified VDR-LBD (VDR-LBDm) (FIG. 5 and FIG. 6) construct is used to assemble a FRET-based assay for measuring 25-hydroxyvitamin D levels. Gene constructs corresponding to the desired VDR-LBDm will be generated such that CFP and YFP are linked at either end. The consequent CFP-VDR-LBDm-YFP or YFP-VDR-LBD-CFP (FIG. 6) constructs can be cloned into appropriate expression vectors to be produced in plant, yeast, bacterial, insect, mammalian or other cells useful for expressing such a construct. CFP-VDR-LBDm-YFP or YFP-VDR-LBDm-CFP proteins can be purified or partially purified from extracts of construct expressing cells and used for assay development.

As described herein, a VDR-LBDm can be constructed which modifies either or both of Ser-237 and Arg-274 with various amino acid side chain groups that will interfere with calcitriol binding but favor that of 25-hydroxyvitamin D. A number of VDR-LBDm constructs can be contemplated which may favor 25-dihydroxyvitamin D binding over that of calcitriol and thus could be used in the FRET based construct for analyzing the presence of 25-dihydroxyvitamin D.

In other embodiments, mutations at the following amino acids are contemplated: Tyr-147, Phe-150, Leu-227, Leu-230, Leu-233, Val-234, Ile-271, Ser-275, Trp-286, Cys-288, Val-300, Leu-309, Leu-313, Val-418, Ser-237, Arg-274, Tyr-143, Ser-278, His-305 and His-397.

FIG. 2 shows a human VDR amino acid sequence and localization of Ser-237 and Arg-274 (bold) as indicated by the arrow. In capitals are amino acids of the ligand binding domain (LBD). FIG. 3 shows the yellow fluorescent protein (SYFP2) amino acid sequence (accession No. AAZ65845) and FIG. 4 shows the cyan fluorescent protein (SCFP3A) amino acid sequence (accession No. AAZ65848). FIG. 5 shows one potential construct according to the invention: in bold; SYFP2, bold+italic; SCFP3A, italic; optional linker, and in the center (normal) VDR-LBD with possible mutations (underlined).

The foregoing description is given for clearness of understanding only, and no unnecessary limitations should be understood therefrom, as modifications within the scope of the invention may be apparent to those having ordinary skill in the art.

Throughout the specification, where compositions are described as including components or materials, it is contemplated that the compositions can also consist essentially of, or consist of, any combination of the recited components or materials, unless described otherwise.

The practice of a method disclosed herein, and individual steps thereof, can be performed manually and/or with the aid of electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

The invention claimed is:

1. A method for measuring the amount or concentration of a vitamin D derivative in a sample comprising:
   a) contacting a sample with a polypeptide comprising a modified VDR ligand-binding domain (VDR-LBD) and a donor-acceptor pair of fluorophores; and
   b) measuring the amount of fluorescence, wherein said amount of fluorescence is detectably higher or lower in the presence of the vitamin D derivative relative to the amount of fluorescence in the absence of the vitamin D derivative;
   wherein the modified VDR comprises at least one mutation causing said modified VDR to have a higher binding affinity to 25-hydroxyvitamin D relative to calcitriol, and wherein said at least one mutation comprises a substitution at one or more amino acid positions selected from the group consisting of 274, 147, 150, 227, 230, 233, 234, 271, 275, 286, 288, 300, 309, 313, 418, 237, 143, 278, 305 and 397 of SEQ ID NO: 1.

2. The method according to claim 1 wherein the vitamin D derivative is 25-hydroxyvitamin D.

3. The method according to claim 2 wherein the modified VDR has at least a 10-fold higher affinity for 25-hydroxyvitamin D than to other vitamin D derivatives.

4. The method according to claim 1 wherein the sample is from a mammalian subject.

5. The method according to claim 4 wherein the mammalian subject is a human.

6. The method according to claim 5 wherein the human is suffering from chronic kidney disease (CKD).

7. The method according to claim 1 wherein said mutation at position 274 comprises a substitution of a basic amino acid residue for an aliphatic amino acid residue.

8. The method according to claim 1 wherein said at least one mutation comprises Arg274Leu.

9. The method according to claim 1 wherein the fluorescence is measured using Fluorescence Resonance Energy Transfer (FRET).

10. The method according to claim 9 wherein the donor-acceptor pair of fluorophores is selected from the group consisting of green fluorescent protein (GFP), red fluorescent protein (RFP), cyan-fluorescent protein (CFP), yellow-fluorescent protein (YFP), and active fragments thereof.

* * * * *

UNITED STATES PATENT AND TRADEMARK OFFICE
CERTIFICATE OF CORRECTION

PATENT NO. : 8,574,862 B2
APPLICATION NO. : 13/318442
DATED : November 5, 2013
INVENTOR(S) : P. Martin Petkovich et al.

It is certified that error appears in the above-identified patent and that said Letters Patent is hereby corrected as shown below:

On the Title Page:

Item (73), "Cytochrama" should be -- Cytochroma --.

Signed and Sealed this
Thirty-first Day of March, 2015

Michelle K. Lee
*Director of the United States Patent and Trademark Office*

SEQUENCE LISTING

```
<160> NUMBER OF SEQ ID NOS: 24

<210> SEQ ID NO 1
<211> LENGTH: 427
<212> TYPE: PRT
<213> ORGANISM: Homo sapiens

<400> SEQUENCE: 1

Met Glu Ala Met Ala Ala Ser Thr Ser Leu Pro Asp Pro Gly Asp Phe
1               5                   10                  15
```

```
Asp Arg Asn Val Pro Arg Ile Cys Gly Val Cys Gly Asp Arg Ala Thr
         20                  25                  30

Gly Phe His Phe Asn Ala Met Thr Cys Glu Gly Cys Lys Gly Phe Phe
         35                  40                  45

Arg Arg Ser Met Lys Arg Lys Ala Leu Phe Thr Cys Pro Phe Asn Gly
 50                  55                  60

Asp Cys Arg Ile Thr Lys Asp Asn Arg Arg His Cys Gln Ala Cys Arg
 65                  70                  75                  80

Leu Lys Arg Cys Val Asp Ile Gly Met Met Lys Glu Phe Ile Leu Thr
                 85                  90                  95

Asp Glu Glu Val Gln Arg Lys Arg Glu Met Ile Leu Lys Arg Lys Glu
                100                 105                 110

Glu Glu Ala Leu Lys Asp Ser Leu Arg Pro Lys Leu Ser Glu Glu Gln
            115                 120                 125

Gln Arg Ile Ile Ala Ile Leu Leu Asp Ala His His Lys Thr Tyr Asp
130                 135                 140

Pro Thr Tyr Ser Asp Phe Cys Gln Phe Arg Pro Pro Val Arg Val Asn
145                 150                 155                 160

Asp Gly Gly Gly Ser His Pro Ser Arg Pro Asn Ser Arg His Thr Pro
                165                 170                 175

Ser Phe Ser Gly Asp Ser Ser Ser Cys Ser Asp His Cys Ile Thr
                180                 185                 190

Ser Ser Asp Met Met Asp Ser Ser Phe Ser Asn Leu Asp Leu Ser
            195                 200                 205

Glu Glu Asp Ser Asp Pro Ser Val Thr Leu Glu Leu Ser Gln Leu
210                 215                 220

Ser Met Leu Pro His Leu Ala Asp Leu Val Ser Tyr Ser Ile Gln Lys
225                 230                 235                 240

Val Ile Gly Phe Ala Lys Met Ile Pro Gly Phe Arg Asp Leu Thr Ser
                245                 250                 255

Glu Asp Gln Ile Val Leu Leu Lys Ser Ser Ala Ile Glu Val Ile Met
            260                 265                 270

Leu Arg Ser Asn Glu Ser Phe Thr Met Asp Asp Met Ser Trp Thr Cys
            275                 280                 285

Gly Asn Gln Asp Tyr Lys Tyr Arg Val Ser Asp Val Thr Lys Ala Gly
290                 295                 300

His Ser Leu Glu Leu Ile Glu Pro Leu Ile Lys Phe Gln Val Gly Leu
305                 310                 315                 320

Lys Lys Leu Asn Leu His Glu Glu Glu His Val Leu Leu Met Ala Ile
                325                 330                 335

Cys Ile Val Ser Pro Asp Arg Pro Gly Val Gln Asp Ala Ala Leu Ile
            340                 345                 350

Glu Ala Ile Gln Asp Arg Leu Ser Asn Thr Leu Gln Thr Tyr Ile Arg
            355                 360                 365

Cys Arg His Pro Pro Gly Ser His Leu Leu Tyr Ala Lys Met Ile
370                 375                 380

Gln Lys Leu Ala Asp Leu Arg Ser Leu Asn Glu Glu His Ser Lys Gln
385                 390                 395                 400

Tyr Arg Cys Leu Ser Phe Gln Pro Glu Cys Ser Met Lys Leu Thr Pro
                405                 410                 415

Leu Val Leu Glu Val Phe Gly Asn Glu Ile Ser
            420                 425
```

<210> SEQ ID NO 2

```
<211> LENGTH: 239
<212> TYPE: PRT
<213> ORGANISM: Artificial Sequence
<220> FEATURE:
<223> OTHER INFORMATION: Synthetic peptide

<400> SEQUENCE: 2

Met Val Ser Lys Gly Glu Glu Leu Phe Thr Gly Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 3
<211> LENGTH: 239
<212> TYPE: PRT
<213> ORGANISM: Artificial Sequence
<220> FEATURE:
<223> OTHER INFORMATION: Synthetic peptide

<400> SEQUENCE: 3

Met Val Ser Lys Gly Glu Glu Leu Phe Thr Gly Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95
```

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Ile Ser Asp Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 4
<211> LENGTH: 740
<212> TYPE: PRT
<213> ORGANISM: Homo sapiens

<400> SEQUENCE: 4

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Leu Ile Cys
        35                  40                  45

Thr Thr Gly Lys Leu Pro Val Pro Trp Pro Thr Leu Val Thr Thr Leu
50                  55                  60

Gly Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Gly Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Lys Leu Ser
        195                 200                 205

Lys Asp Pro Asn Glu Lys Arg Asp His Met Val Leu Leu Glu Phe Val
210                 215                 220

Thr Ala Ala Gly Ile Thr Leu Gly Met Asp Glu Leu Tyr Lys Asp Ser
225                 230                 235                 240
```

-continued

```
Leu Arg Pro Lys Leu Ser Glu Glu Gln Arg Ile Ile Ala Ile Leu
                245                 250                 255

Leu Asp Ala His His Lys Thr Tyr Asp Pro Thr Tyr Ser Asp Phe Cys
                260                 265                 270

Gln Phe Arg Pro Pro Val Arg Val Asn Asp Gly Gly Ser Val Thr
            275                 280                 285

Leu Glu Leu Ser Gln Leu Ser Met Leu Pro His Leu Ala Asp Leu Val
            290                 295                 300

Ser Tyr Ser Ile Gln Lys Val Ile Gly Phe Ala Lys Met Ile Pro Gly
305                 310                 315                 320

Phe Arg Asp Leu Thr Ser Glu Asp Gln Ile Val Leu Leu Lys Ser Ser
                325                 330                 335

Ala Ile Glu Val Ile Met Leu Arg Ser Asn Glu Ser Phe Thr Met Asp
                340                 345                 350

Asp Met Ser Trp Thr Cys Gly Asn Gln Asp Tyr Lys Tyr Arg Val Ser
                355                 360                 365

Asp Val Thr Lys Ala Gly His Ser Leu Glu Leu Ile Glu Pro Leu Ile
            370                 375                 380

Lys Phe Gln Val Gly Leu Lys Lys Leu Asn Leu His Glu Glu Glu His
385                 390                 395                 400

Val Leu Leu Met Ala Ile Cys Ile Val Ser Pro Asp Arg Pro Gly Val
                405                 410                 415

Gln Asp Ala Ala Leu Ile Glu Ala Ile Gln Asp Arg Leu Ser Asn Thr
            420                 425                 430

Leu Gln Thr Tyr Ile Arg Cys Arg His Pro Pro Gly Ser His Leu
            435                 440                 445

Leu Tyr Ala Lys Met Ile Gln Lys Leu Ala Asp Leu Arg Ser Leu Asn
            450                 455                 460

Glu Glu His Ser Lys Gln Tyr Arg Cys Leu Ser Phe Gln Pro Glu Cys
465                 470                 475                 480

Ser Met Lys Leu Thr Pro Leu Val Leu Glu Val Phe Gly Asn Glu Ile
                485                 490                 495

Ser Gly Ser Gly Thr Gly Val Ser Lys Gly Glu Glu Leu Phe Thr Gly
                500                 505                 510

Val Val Pro Ile Leu Val Glu Leu Asp Gly Asp Val Asn Gly His Lys
                515                 520                 525

Phe Ser Val Ser Gly Glu Gly Glu Gly Asp Ala Thr Tyr Gly Lys Leu
530                 535                 540

Thr Leu Lys Phe Ile Cys Thr Thr Gly Lys Leu Pro Val Pro Trp Pro
545                 550                 555                 560

Thr Leu Val Thr Thr Leu Thr Trp Gly Val Gln Cys Phe Ala Arg Tyr
                565                 570                 575

Pro Asp His Met Lys Gln His Asp Phe Phe Lys Ser Ala Met Pro Glu
                580                 585                 590

Gly Tyr Val Gln Glu Arg Thr Ile Phe Phe Lys Asp Asp Gly Asn Tyr
                595                 600                 605

Lys Thr Arg Ala Glu Val Lys Phe Glu Gly Asp Thr Leu Val Asn Arg
            610                 615                 620

Ile Glu Leu Lys Gly Ile Asp Phe Lys Glu Asp Gly Asn Ile Leu Gly
625                 630                 635                 640

His Lys Leu Glu Tyr Asn Tyr Ile Ser Asp Asn Val Tyr Ile Thr Ala
                645                 650                 655
```

```
Asp Lys Gln Lys Asn Gly Ile Lys Ala Asn Phe Lys Ile Arg His Asn
                660                 665                 670

Ile Glu Asp Gly Gly Val Gln Leu Ala Asp His Tyr Gln Gln Asn Thr
            675                 680                 685

Pro Ile Gly Asp Gly Pro Val Leu Leu Pro Asn His Tyr Leu Ser
690                 695                 700

Thr Gln Ser Lys Leu Ser Lys Asp Pro Asn Glu Lys Arg Asp His Met
705                 710                 715                 720

Val Leu Leu Glu Phe Val Thr Ala Ala Gly Ile Thr Leu Gly Met Asp
                725                 730                 735

Glu Leu Tyr Lys
            740

<210> SEQ ID NO 5
<211> LENGTH: 69
<212> TYPE: PRT
<213> ORGANISM: Homo sapiens

<400> SEQUENCE: 5

Gln Ile Cys Arg Val Cys Gly Asp Lys Ala Thr Gly Tyr His Phe Asn
1               5                   10                  15

Val Met Thr Cys Glu Gly Cys Lys Gly Phe Phe Arg Arg Ala Met Lys
            20                  25                  30

Arg Asn Ala Arg Leu Arg Cys Pro Phe Arg Lys Gly Ala Cys Glu Ile
        35                  40                  45

Thr Arg Lys Thr Arg Arg Gln Cys Gln Ala Cys Arg Leu Arg Lys Cys
    50                  55                  60

Leu Glu Ser Gly Met
65

<210> SEQ ID NO 6
<211> LENGTH: 68
<212> TYPE: PRT
<213> ORGANISM: Gallus gallus

<400> SEQUENCE: 6

Lys Val Cys Ala Val Cys Gly Asp Arg Ala Thr Gly Tyr His Phe His
1               5                   10                  15

Val Met Ser Cys Glu Gly Cys Lys Gly Phe Phe Arg Arg Ser Ile Leu
            20                  25                  30

Lys Gly Val His Phe Thr Cys Pro Phe Thr Arg Ser Cys Pro Ile Thr
        35                  40                  45

Lys Ala Lys Arg Arg Gln Cys Gln Ala Cys Arg Leu Gln Lys Cys Leu
    50                  55                  60

Asp Val Gly Met
65

<210> SEQ ID NO 7
<211> LENGTH: 68
<212> TYPE: PRT
<213> ORGANISM: Fugu rubripes

<400> SEQUENCE: 7

Arg Ala Cys Gly Val Cys Gly Asp Gln Ala Lys Gly Tyr His Phe Asn
1               5                   10                  15

Ala Trp Thr Cys Glu Gly Cys Lys Gly Phe Phe Arg Arg Ala Ile Lys
            20                  25                  30

Arg Thr Pro Pro Leu Pro Cys Gln Phe Leu Asn Lys Cys Ser Ile Thr
        35                  40                  45
```

```
Lys Lys Asn Arg Arg Gln Cys Gln Asp Cys Arg Leu Arg Lys Cys Gln
     50                  55                  60

Ala Ile Gly Met
 65
```

<210> SEQ ID NO 8
<211> LENGTH: 68
<212> TYPE: PRT
<213> ORGANISM: Homo sapiens

<400> SEQUENCE: 8

```
Arg Ile Cys Gly Val Cys Gly Asp Arg Ala Thr Gly Phe His Phe Asn
 1               5                  10                  15

Ala Met Thr Cys Glu Gly Cys Lys Gly Phe Phe Arg Arg Ser Met Lys
                20                  25                  30

Arg Lys Ala Leu Phe Thr Cys Pro Phe Asn Gly Asp Cys Arg Ile Thr
             35                  40                  45

Lys Asp Asn Arg Arg His Cys Gln Ala Cys Arg Leu Lys Arg Cys Val
     50                  55                  60

Asp Ile Gly Met
 65
```

<210> SEQ ID NO 9
<211> LENGTH: 68
<212> TYPE: PRT
<213> ORGANISM: Mus musculus

<400> SEQUENCE: 9

```
Arg Ile Cys Gly Val Cys Gly Asp Arg Ala Thr Gly Phe His Phe Asn
 1               5                  10                  15

Ala Met Thr Cys Glu Gly Cys Lys Gly Phe Phe Arg Arg Ser Met Lys
                20                  25                  30

Arg Lys Ala Leu Phe Thr Cys Pro Phe Asn Gly Asp Cys Arg Ile Thr
             35                  40                  45

Lys Asp Asn Arg Arg His Cys Gln Ala Cys Arg Leu Lys Arg Cys Val
     50                  55                  60

Asp Ile Gly Met
 65
```

<210> SEQ ID NO 10
<211> LENGTH: 68
<212> TYPE: PRT
<213> ORGANISM: Xenopus laevis

<400> SEQUENCE: 10

```
Arg Ile Cys Gly Val Cys Gly Asp Lys Ala Thr Gly Phe His Phe Asn
 1               5                  10                  15

Ala Met Thr Cys Glu Gly Cys Lys Gly Phe Phe Arg Arg Ser Met Lys
                20                  25                  30

Arg Lys Ala Met Phe Thr Cys Pro Phe Asn Gly Asp Cys Arg Ile Thr
             35                  40                  45

Lys Asp Asn Arg Arg His Cys Gln Ser Cys Arg Leu Lys Arg Cys Val
     50                  55                  60

Asp Ile Gly Met
 65
```

<210> SEQ ID NO 11
<211> LENGTH: 68
<212> TYPE: PRT

<213> ORGANISM: Danio rerio

<400> SEQUENCE: 11

Pro Ile Cys Gly Val Cys Gly Asp Lys Ala Thr Gly Phe His Phe Asn
1               5                   10                  15

Ala Met Thr Cys Glu Gly Cys Lys Gly Phe Phe Arg Arg Ser Met Lys
            20                  25                  30

Arg Lys Ala Ser Phe Thr Cys Pro Phe Asn Gly Asn Cys Thr Ile Thr
        35                  40                  45

Lys Asp Asn Arg Arg His Cys Gln Ala Cys Arg Leu Lys Arg Cys Ile
50                  55                  60

Asp Ile Gly Met
65

<210> SEQ ID NO 12
<211> LENGTH: 68
<212> TYPE: PRT
<213> ORGANISM: Petromyzon marinus

<400> SEQUENCE: 12

Lys Val Cys Gly Val Cys Gly Asp Lys Ala Thr Gly Tyr His Phe Asn
1               5                   10                  15

Ala Met Thr Cys Glu Gly Cys Lys Gly Phe Phe Arg Arg Ser Met Lys
            20                  25                  30

Arg Ser Ala Ser Phe Thr Cys Pro Phe Glu Gly Lys Cys Asn Ile Thr
        35                  40                  45

Lys Asp Asn Arg Arg His Cys Gln Ala Cys Arg Leu Lys Arg Cys Arg
50                  55                  60

Asp Ile Gly Met
65

<210> SEQ ID NO 13
<211> LENGTH: 56
<212> TYPE: PRT
<213> ORGANISM: Ciona intestinalis

<400> SEQUENCE: 13

Met His Phe Gly Ala Ile Thr Cys Glu Gly Cys Lys Gly Phe Phe Arg
1               5                   10                  15

Arg Ser Val Lys Lys Asn Ala Ser Phe Ser Cys Ala Phe Glu Lys Lys
            20                  25                  30

Cys Glu Ile Asn Lys Asn Asn Arg Lys His Cys Gln Ala Cys Arg Phe
        35                  40                  45

Asn Ala Cys Leu Ala Ala Gly Met
    50                  55

<210> SEQ ID NO 14
<211> LENGTH: 68
<212> TYPE: PRT
<213> ORGANISM: Homo sapiens

<400> SEQUENCE: 14

Arg Asn Cys Val Val Cys Gly Asp Gln Ala Thr Gly Tyr His Phe Asn
1               5                   10                  15

Ala Leu Thr Cys Glu Gly Cys Lys Gly Phe Phe Arg Arg Thr Val Ser
            20                  25                  30

Lys Ser Ile Gly Pro Thr Cys Pro Phe Ala Gly Ser Cys Glu Val Ser
        35                  40                  45

```
Lys Thr Gln Arg Arg His Cys Pro Ala Cys Arg Leu Gln Lys Cys Leu
         50                  55                  60

Asp Ala Gly Met
 65

<210> SEQ ID NO 15
<211> LENGTH: 294
<212> TYPE: PRT
<213> ORGANISM: Homo sapiens

<400> SEQUENCE: 15

Gln Gly Leu Thr Glu Glu Gln Arg Met Met Ile Arg Glu Leu Met Asp
  1               5                  10                  15

Ala Gln Met Lys Thr Phe Asp Thr Thr Phe Ser His Phe Lys Asn Phe
             20                  25                  30

Arg Leu Pro Gly Val Leu Ser Ser Gly Cys Glu Leu Pro Glu Ser Leu
         35                  40                  45

Gln Ala Pro Ser Arg Glu Ala Ala Lys Trp Ser Gln Val Arg Lys
     50                  55                  60

Asp Leu Cys Ser Leu Lys Val Ser Leu Gln Leu Arg Gly Glu Asp Gly
 65                  70                  75                  80

Ser Val Trp Asn Tyr Lys Pro Pro Ala Asp Ser Gly Gly Lys Glu Ile
                 85                  90                  95

Phe Ser Leu Leu Pro His Met Ala Asp Met Ser Thr Tyr Met Phe Lys
                100                 105                 110

Gly Ile Ile Ser Phe Ala Lys Val Ile Ser Tyr Phe Arg Asp Leu Pro
            115                 120                 125

Ile Glu Asp Gln Ile Ser Leu Leu Lys Gly Ala Ala Phe Glu Leu Cys
        130                 135                 140

Gln Leu Arg Phe Asn Thr Val Phe Asn Ala Glu Thr Gly Thr Trp Glu
145                 150                 155                 160

Cys Gly Arg Leu Ser Tyr Cys Leu Glu Asp Thr Ala Gly Gly Phe Gln
                165                 170                 175

Gln Leu Leu Leu Glu Pro Met Leu Lys Phe His Tyr Met Leu Lys Lys
            180                 185                 190

Leu Gln Leu His Glu Glu Glu Tyr Val Leu Met Gln Ala Ile Ser Leu
        195                 200                 205

Phe Ser Pro Asp Arg Pro Gly Val Leu Gln His Arg Val Ile Asp Gln
    210                 215                 220

Leu Gln Glu Gln Phe Ala Ile Thr Leu Lys Ser Tyr Ile Glu Cys Asn
225                 230                 235                 240

Arg Pro Gln Pro Ala His Arg Phe Leu Phe Leu Lys Ile Met Ala Met
                245                 250                 255

Leu Thr Glu Leu Arg Ser Ile Asn Ala Gln His Thr Gln Arg Leu Leu
            260                 265                 270

Arg Ile Gln Asp Ile His Pro Phe Ala Thr Pro Leu Met Gln Glu Leu
        275                 280                 285

Phe Gly Ile Thr Gly Ser
    290

<210> SEQ ID NO 16
<211> LENGTH: 267
<212> TYPE: PRT
<213> ORGANISM: Gallus gallus

<400> SEQUENCE: 16
```

```
Gly Gly Leu Thr Ala Glu Gln Gln Glu Leu Ile Ser Ile Leu Ile Ala
1               5                   10                  15

Ala His Lys Arg Thr Phe Asp Ser Phe Ser Gln Phe Gln His Tyr
            20                  25                  30

Gln Pro Ala Val Arg Leu Cys Ile Pro Gly Pro Cys Ser Gln Ser Pro
            35                  40                  45

Pro Gly Pro Gly Val Pro Ser Ala Ser Leu Ser Pro Gln Leu Asp Cys
50                      55                  60

Leu Asp Glu Asp Val Leu Pro Asp Val Phe Ser Ile Leu Pro His Phe
65                  70                  75                  80

Ala Asp Leu Ser Thr Phe Met Ile Gln Gln Val Ile Lys Phe Ala Lys
                85                  90                  95

Glu Ile Pro Ala Phe Arg Gly Leu Pro Ile Asp Asp Gln Ile Ser Leu
            100                 105                 110

Leu Lys Gly Ala Thr Leu Gly Ile Cys Gln Ile Gln Phe Asn Thr Val
            115                 120                 125

Phe Asn Glu Glu Thr Asn Ala Trp Glu Cys Gly Gln His Cys Phe Thr
            130                 135                 140

Ile Lys Asp Gly Ala Leu Ala Gly Phe Gln Gln Ile Tyr Leu Glu Pro
145                 150                 155                 160

Leu Leu Lys Phe His Ile Ser Leu Lys Lys Leu Arg Leu His Glu Ala
                165                 170                 175

Glu Tyr Val Leu Leu Val Ala Met Leu Leu Phe Ser Pro Asp His Ala
            180                 185                 190

Ser Val Thr Gln Arg Asp Phe Ile Asp Gln Leu Gln Lys Val Ala
            195                 200                 205

Leu Thr Leu Lys Ser Tyr Ile Asp His Arg His Pro Met Pro Glu Gly
210                 215                 220

Arg Phe Leu Tyr Ala Lys Leu Leu Leu Leu Thr Glu Leu Gln Thr
225                 230                 235                 240

Leu Lys Met Glu Asn Thr Arg Gln Ile Leu His Ile Gln Asp Leu Ser
                245                 250                 255

Ser Met Thr Pro Leu Leu Ser Glu Ile Ile Ser
            260                 265

<210> SEQ ID NO 17
<211> LENGTH: 295
<212> TYPE: PRT
<213> ORGANISM: Fugu rubripes

<400> SEQUENCE: 17

Ile His Leu Ser Ser Gln Gln Glu Glu Thr Ile Arg Glu Leu Leu Tyr
1               5                   10                  15

Gly His Arg Lys Thr Phe Asp Leu Glu Phe Tyr Arg Phe Ser Ser Phe
            20                  25                  30

Arg Val Arg Thr Ser Thr Thr Leu Phe Asp Leu Ser Lys Ser Leu Ser
            35                  40                  45

Glu Arg Leu Asn Ile Phe Ala Val Arg Gly Ser Ser Pro Ser Gly Pro
50                  55                  60

Ala Ser Ser Asp Val Ser Ser Leu Ser Thr Ser Ala Arg Leu Arg Gly
65                  70                  75                  80

Arg Pro Glu Thr Pro Gln Thr Gln Gly Gly Glu Asn Ala Arg Arg Gly
                85                  90                  95

Cys Val Phe Thr Ala Leu Pro His Val Thr Asp Leu Ala Thr Cys Met
            100                 105                 110
```

```
Ile His Asp Ile Ile Ala Phe Ser Lys Ser Leu Thr Asp Phe Lys Ser
    115                 120                 125

Leu Leu Ile Gly Asp Gln Ile Ala Leu Leu Lys Gly Ala Thr Phe Glu
130                 135                 140

Val Met Glu Ile Arg Phe Asn Met Val Phe Asn Thr Lys Thr Gly Leu
145                 150                 155                 160

Trp Glu Cys Gly His Ala Thr Tyr Cys Ile Glu Asp Ala Val Arg Ala
                165                 170                 175

Gly Phe Gln Pro Leu Phe Leu Glu Pro Leu Leu Lys Phe His His Thr
            180                 185                 190

Leu Arg Asn Leu Gly Leu Glu Glu Glu Tyr Val Leu Met Gln Ala
        195                 200                 205

Leu Ser Leu Phe Ser Pro Asp Arg Pro Gly Val Gln Gln His Ser Val
    210                 215                 220

Ile Asp Lys Ile His Glu Asn Leu Ala Leu Ala Leu Lys Thr Arg Ile
225                 230                 235                 240

Glu Leu Lys Arg Thr Gly Pro Glu Lys His Met Leu Tyr Pro Lys Val
                245                 250                 255

Leu Ser Cys Leu Thr Glu Met Arg Thr Met Asn Glu Gly Tyr Ser Lys
            260                 265                 270

Gln Val Leu Gln Ile Gln Asp Ile Gln Pro Asn Val Val Ile Pro Pro
        275                 280                 285

Leu Leu Met Glu Met Val Ser
    290                 295

<210> SEQ ID NO 18
<211> LENGTH: 306
<212> TYPE: PRT
<213> ORGANISM: Homo sapiens

<400> SEQUENCE: 18

Pro Lys Leu Ser Glu Gln Gln Arg Ile Ile Ala Ile Leu Leu Asp
1               5                   10                  15

Ala His His Lys Thr Tyr Asp Pro Thr Tyr Ser Asp Phe Cys Gln Phe
                20                  25                  30

Arg Pro Pro Val Arg Val Asn Asp Gly Gly Ser His Pro Ser Arg
            35                  40                  45

Pro Asn Ser Arg His Thr Pro Ser Phe Ser Gly Asp Ser Ser Ser
    50                  55                  60

Cys Ser Asp His Cys Ile Thr Ser Ser Asp Met Met Asp Ser Ser Ser
65                  70                  75                  80

Phe Ser Asn Leu Asp Leu Ser Glu Glu Asp Ser Asp Pro Ser Val
                85                  90                  95

Thr Leu Glu Leu Ser Gln Leu Ser Met Leu Pro His Leu Ala Asp Leu
            100                 105                 110

Val Ser Tyr Ser Ile Gln Lys Val Ile Gly Phe Ala Lys Met Ile Pro
    115                 120                 125

Gly Phe Arg Asp Leu Thr Ser Glu Asp Gln Ile Val Leu Leu Lys Ser
130                 135                 140

Ser Ala Ile Glu Val Ile Met Leu Arg Ser Asn Glu Ser Phe Thr Met
145                 150                 155                 160

Asp Asp Met Ser Trp Thr Cys Gly Asn Gln Asp Tyr Lys Tyr Arg Val
                165                 170                 175

Ser Asp Val Thr Lys Ala Gly His Ser Leu Glu Leu Ile Glu Pro Leu
            180                 185                 190
```

```
Ile Lys Phe Gln Val Gly Leu Lys Lys Leu Asn Leu His Glu Glu
        195                 200                 205
His Val Leu Leu Met Ala Ile Cys Ile Val Ser Pro Asp Arg Pro Gly
210                 215                 220
Val Gln Asp Ala Ala Leu Ile Glu Ala Ile Gln Asp Arg Leu Ser Asn
225                 230                 235                 240
Thr Leu Gln Thr Tyr Ile Arg Cys Arg His Pro Pro Gly Ser His
            245                 250                 255
Leu Leu Tyr Ala Lys Met Ile Gln Lys Leu Ala Asp Leu Arg Ser Leu
                260                 265                 270
Asn Glu Glu His Ser Lys Gln Tyr Arg Cys Leu Ser Phe Gln Pro Glu
            275                 280                 285
Cys Ser Met Lys Leu Thr Pro Leu Val Leu Glu Val Phe Gly Asn Glu
290                 295                 300
Ile Ser
305

<210> SEQ ID NO 19
<211> LENGTH: 302
<212> TYPE: PRT
<213> ORGANISM: Mus musculus

<400> SEQUENCE: 19

Pro Lys Leu Ser Glu Glu Gln Gln His Ile Ile Ala Ile Leu Leu Asp
1               5                   10                  15
Ala His His Lys Thr Tyr Asp Pro Thr Tyr Ala Asp Phe Arg Asp Phe
                20                  25                  30
Arg Pro Pro Ile Arg Ala Asp Val Ala Thr Gly Ser Tyr Ser Pro Arg
            35                  40                  45
Pro Thr Leu Ser Phe Ser Gly Asp Ser Ser Asn Ser Asp Leu Tyr
        50                  55                  60
Thr Pro Ser Leu Asp Met Met Glu Pro Ala Ser Phe Ser Thr Met Asp
65                  70                  75                  80
Leu Asn Glu Glu Gly Ser Asp Asp Pro Ser Val Thr Leu Asp Leu Ser
                85                  90                  95
Pro Leu Ser Met Leu Pro His Leu Ala Asp Leu Val Ser Tyr Ser Ile
            100                 105                 110
Gln Lys Val Ile Gly Phe Ala Lys Met Ile Pro Gly Phe Arg Asp Leu
        115                 120                 125
Thr Ser Asp Asp Gln Ile Val Leu Leu Lys Ser Ser Ala Ile Glu Val
130                 135                 140
Ile Met Leu Arg Ser Asn Gln Ser Phe Thr Met Asp Asp Met Ser Trp
145                 150                 155                 160
Asp Cys Gly Ser Gln Asp Tyr Lys Tyr Asp Ile Thr Asp Val Ser Arg
                165                 170                 175
Ala Gly His Thr Leu Glu Leu Ile Glu Pro Leu Ile Lys Phe Gln Val
            180                 185                 190
Gly Leu Lys Lys Leu Asn Leu His Glu Glu His Val Leu Leu Met
        195                 200                 205
Ala Ile Cys Ile Val Ser Pro Asp Arg Pro Gly Val Gln Asp Ala Lys
210                 215                 220
Leu Val Glu Ala Ile Gln Asp Arg Leu Ser Asn Thr Leu Gln Thr Tyr
225                 230                 235                 240
Ile Arg Cys Arg His Pro Pro Pro Gly Ser His Gln Leu Tyr Ala Lys
                245                 250                 255
```

```
Met Ile Gln Lys Leu Ala Asp Leu Arg Ser Leu Asn Glu Glu His Ser
            260                 265                 270

Lys Gln Tyr Arg Ser Leu Ser Phe Gln Pro Glu Asn Ser Ser Met Lys
        275                 280                 285

Leu Thr Pro Leu Val Leu Glu Val Phe Gly Asn Glu Ile Ser
    290                 295                 300

<210> SEQ ID NO 20
<211> LENGTH: 301
<212> TYPE: PRT
<213> ORGANISM: Xenopus laevis

<400> SEQUENCE: 20

Pro Lys Ile Ser Asp Glu Gln Gln Lys Met Ile Asp Ile Leu Leu Glu
1               5                  10                  15

Ala His Arg Lys Thr Phe Asp Thr Thr Tyr Ser Asp Phe Asn Lys Phe
            20                  25                  30

Arg Pro Pro Val Arg Glu Asn Val Asp Pro Phe Arg Arg Ile Thr Arg
        35                  40                  45

Ser Ser Ser Val His Thr Gln Gly Ser Pro Ser Glu Asp Ser Asp Val
    50                  55                  60

Phe Thr Ser Ser Pro Asp Ser Ser Glu His Gly Phe Phe Ser Ala Ser
65                  70                  75                  80

Leu Phe Gly Gln Phe Glu Tyr Ser Ser Met Gly Gly Lys Ser Gly Glu
                85                  90                  95

Leu Ser Met Leu Pro His Ile Ala Asp Leu Val Ser Tyr Ser Ile Gln
            100                 105                 110

Lys Ile Ile Gly Phe Ala Lys Met Ile Pro Gly Phe Arg Asp Leu Ile
        115                 120                 125

Ala Glu Asp Gln Ile Ala Leu Leu Lys Ser Ser Val Ile Glu Val Ile
    130                 135                 140

Met Leu Arg Ser Asn Gln Ser Phe Ser Leu Asp Asp Met Ser Trp Thr
145                 150                 155                 160

Cys Gly Ser Glu Asp Phe Lys Tyr Lys Val Asp Asp Val Thr Gln Ala
                165                 170                 175

Gly His Asn Met Glu Leu Leu Glu Pro Leu Val Lys Phe Gln Val Gly
            180                 185                 190

Leu Lys Lys Leu Asp Leu His Glu Glu Glu His Val Leu Leu Met Ala
        195                 200                 205

Ile Cys Ile Leu Ser Pro Asp Arg Pro Gly Leu Gln Asp Lys Ala Leu
    210                 215                 220

Val Glu Ser Ile Gln Asp Arg Leu Ser Ser Thr Leu Gln Thr Tyr Ile
225                 230                 235                 240

Leu Cys Lys His Pro Pro Gly Ser Arg Leu Leu Tyr Ala Lys Met
                245                 250                 255

Ile Gln Lys Leu Ala Asp Leu Arg Ser Leu Asn Glu Glu His Ser Lys
            260                 265                 270

Gln Tyr Arg Ser Ile Ser Phe Leu Pro Glu His Ser Ser Met Lys Leu
        275                 280                 285

Thr Pro Leu Met Leu Glu Val Phe Ser Asp Glu Ile Pro
    290                 295                 300

<210> SEQ ID NO 21
<211> LENGTH: 300
<212> TYPE: PRT
<213> ORGANISM: Danio rerio
```

<400> SEQUENCE: 21

Pro Arg Leu Ser Asp Glu Gln Met Gln Ile Ile Asn Ser Leu Val Glu
1               5                   10                  15

Ala His His Lys Thr Tyr Asp Asp Ser Tyr Ser Asp Phe Val Arg Phe
                20                  25                  30

Arg Pro Pro Val Arg Glu Gly Pro Val Thr Arg Ser Ala Ser Arg Ala
            35                  40                  45

Ala Ser Leu His Ser Leu Ser Asp Ala Ser Ser Asp Ser Phe Asn His
        50                  55                  60

Ser Pro Glu Ser Val Asp Thr Lys Leu Asn Phe Ser Asn Leu Leu Met
65                  70                  75                  80

Met Tyr Gln Asp Ser Gly Ser Pro Asp Ser Ser Glu Glu Asp Gln Gln
                85                  90                  95

Ser Arg Leu Ser Met Leu Pro His Leu Ala Asp Leu Val Ser Tyr Ser
            100                 105                 110

Ile Gln Lys Val Ile Gly Phe Ala Lys Met Ile Pro Gly Phe Arg Asp
        115                 120                 125

Leu Thr Ala Glu Asp Gln Ile Ala Leu Leu Lys Ser Ser Ala Ile Glu
130                 135                 140

Ile Ile Met Leu Arg Ser Asn Gln Ser Phe Ser Leu Glu Asp Met Ser
145                 150                 155                 160

Trp Ser Cys Gly Gly Pro Asp Phe Lys Tyr Cys Ile Asn Asp Val Thr
                165                 170                 175

Lys Ala Gly His Thr Leu Glu Leu Leu Glu Pro Leu Val Lys Phe Gln
            180                 185                 190

Val Gly Leu Lys Lys Leu Lys Leu His Glu Glu Glu His Val Leu Leu
        195                 200                 205

Met Ala Ile Cys Leu Leu Ser Pro Asp Arg Pro Gly Val Gln Asp His
210                 215                 220

Val Arg Ile Glu Ala Leu Gln Asp Arg Leu Cys Asp Val Leu Gln Ala
225                 230                 235                 240

Tyr Ile Arg Ile Gln His Pro Gly Gly Arg Leu Leu Tyr Ala Lys Met
                245                 250                 255

Ile Gln Lys Leu Ala Asp Leu Arg Ser Leu Asn Glu Glu His Ser Lys
            260                 265                 270

Gln Tyr Arg Ser Leu Ser Phe Gln Pro Glu His Ser Met Gln Leu Thr
        275                 280                 285

Pro Leu Val Leu Glu Val Phe Gly Ser Glu Val Ser
290                 295                 300

<210> SEQ ID NO 22
<211> LENGTH: 282
<212> TYPE: PRT
<213> ORGANISM: Petromyzon marinus

<400> SEQUENCE: 22

Pro Gln Leu Leu Glu Glu Gln Glu Arg Leu Ile Ala Thr Leu Ile Glu
1               5                   10                  15

Ala His Arg Lys Thr Tyr Asp Ala Ser Tyr Ser Asp Phe Ser Gln Phe
                20                  25                  30

Arg Pro Pro Lys Arg Gly Asp Gly Ser Pro Glu Cys Arg Asn Ala Thr
            35                  40                  45

Asn Pro Phe Leu Met Ser Leu Leu Asn Ser Asp Met Asp Glu Leu Pro
        50                  55                  60

```
Lys Ala Ser Ala Ser Gly Ala Glu Ala Ala Gly Asp Glu Leu Ser
 65                  70                  75                  80

Met Leu Pro His Leu Ala Asp Leu Val Ser Tyr Ser Ile Gln Lys Val
                 85                  90                  95

Ile Gly Phe Ala Lys Met Ile Pro Gly Phe Lys Glu Leu Cys Thr Glu
                100                 105                 110

Asp Gln Ile Ser Leu Leu Lys Ala Ser Ala Ile Glu Ile Ile Leu
                115                 120                 125

Arg Ser Asn Glu Ser Phe Thr Met Glu Asp Asn Ser Trp Thr Cys Gly
        130                 135                 140

Ser Asn Glu Phe Lys Tyr Gln Ile Gly Asp Val Met Gln Ala Gly His
145                 150                 155                 160

Lys Leu Glu Leu Leu Glu Pro Leu Val Lys Phe Gln Val Asn Met Lys
                165                 170                 175

Lys Leu Asp Leu His Glu Ala Glu His Val Leu Leu Met Ala Ile Cys
                180                 185                 190

Leu Phe Ser Pro Asp Arg Pro Gly Val Gln Asp Arg Cys Arg Val Glu
            195                 200                 205

Glu Val Gln Glu His Leu Thr Glu Thr Leu Arg Ala Tyr Ile Ala Cys
210                 215                 220

Arg His Pro Leu Ser Cys Lys His Met Leu Tyr Thr Lys Met Val Glu
225                 230                 235                 240

Lys Leu Thr Glu Leu Arg Ser Leu Asn Glu Glu His Ser Lys Gln Tyr
                245                 250                 255

Leu Gln Ile Ser Gln Asp Ala Val Asn Lys Glu Asp Leu Pro Pro Leu
            260                 265                 270

Leu Leu Glu Val Phe Gly Asn Pro Thr Ala
            275                 280

<210> SEQ ID NO 23
<211> LENGTH: 303
<212> TYPE: PRT
<213> ORGANISM: Ciona intestinalis

<400> SEQUENCE: 23

Thr Arg Met Thr Met Asp Glu Lys Leu Leu Val Lys Thr Leu Leu Lys
 1               5                  10                  15

Gly His Arg Asp Ser Tyr Asp Phe Ala Tyr Val Glu Tyr Asp Thr Phe
                20                  25                  30

Arg Gly Arg Glu Pro Gly Ser Asn Asp Gly Gln Gln Glu Ile Gly Asn
            35                  40                  45

Asn Thr Glu Asn Pro Asn Gly Leu Asp Ala Ala Thr Ala Val Glu Ala
 50                  55                  60

Gln Ser Thr Thr Glu Asp Ser Gly Lys Gln Leu His Leu Met Leu Leu
 65                  70                  75                  80

Phe Gln His Phe Leu Pro Ile Tyr Pro Phe Ser Phe Asp Pro Lys Ala
                 85                  90                  95

Lys Gln Leu Phe Gln His Phe Cys Asp Ile Met Thr Trp Gly Ile Arg
                100                 105                 110

Lys Val Ile Asp Tyr Cys Lys Gly Ile Pro Gln Phe Val Gln Leu Ser
                115                 120                 125

Ile Val Asp Gln Ile Val Leu Leu Arg Gly Gly Cys Leu Glu Met Leu
            130                 135                 140

Val Leu Arg Ser Tyr Phe Ala Phe Ser Cys Asn Glu Asn Lys Tyr Met
145                 150                 155                 160
```

```
Ser Asp Lys Phe Gln Tyr Lys Pro Ser Asp Phe Leu Gln Ala Gly Gly
            165                 170                 175

Asn Lys Glu Phe Val Glu Lys Tyr Asn Ser Leu His Ile Arg Met Arg
        180                 185                 190

Lys Met Lys Leu Gln Val Glu Glu Ile Cys Leu Leu Leu Ala Leu Val
    195                 200                 205

Leu Phe Ser Pro Asp Arg Pro Gly Leu Glu Asp Gln Ala Lys Val Glu
210                 215                 220

Gln Met Gln Asp Cys Val Ala Asn Thr Leu Gln Ala Tyr Glu Tyr Thr
225                 230                 235                 240

His Lys Pro Pro Asn Glu Ser Ser Phe Leu Gln Ala Arg Thr Met Tyr
                245                 250                 255

Cys Glu Leu Leu Leu Ile Leu Pro Ile Leu Arg Thr Ile Asn Met Leu
                260                 265                 270

Phe Ala Gln Asn Ile Met Ser Leu Lys Gln Thr Asn Glu Lys Asp Met
                275                 280                 285

Asn Pro Leu Ile Leu Glu Val Asn Asn Ser Ala Asp Asp Glu Asp
                290                 295                 300

<210> SEQ ID NO 24
<211> LENGTH: 245
<212> TYPE: PRT
<213> ORGANISM: Homo sapiens

<400> SEQUENCE: 24

Val Gln Leu Ser Lys Glu Gln Glu Leu Ile Arg Thr Leu Leu Gly
1               5                   10                  15

Ala His Thr Arg His Met Gly Thr Met Phe Gln Phe Val Gln Phe
                20                  25                  30

Arg Pro Pro Ala His Leu Phe Ile His His Gln Pro Leu Pro Thr Leu
                35                  40                  45

Ala Pro Val Leu Pro Leu Val Thr His Phe Ala Asp Ile Asn Thr Phe
            50                  55                  60

Met Val Leu Gln Val Ile Lys Phe Thr Lys Asp Leu Pro Val Phe Arg
65                  70                  75                  80

Ser Leu Pro Ile Glu Asp Gln Ile Ser Leu Leu Lys Gly Ala Ala Val
                85                  90                  95

Glu Ile Cys His Ile Val Leu Asn Thr Thr Phe Cys Leu Gln Thr Gln
                100                 105                 110

Asn Phe Leu Cys Gly Pro Leu Arg Tyr Thr Ile Glu Asp Gly Ala Arg
            115                 120                 125

Val Gly Phe Gln Val Glu Phe Leu Glu Leu Leu Phe His Phe His Gly
        130                 135                 140

Thr Leu Arg Lys Leu Gln Leu Gln Glu Pro Glu Tyr Val Leu Leu Ala
145                 150                 155                 160

Ala Met Ala Leu Phe Ser Pro Asp Arg Pro Gly Val Thr Gln Arg Asp
                165                 170                 175

Glu Ile Asp Gln Leu Gln Glu Glu Met Ala Leu Thr Leu Gln Ser Tyr
            180                 185                 190

Ile Lys Gly Gln Gln Arg Arg Pro Arg Asp Arg Phe Leu Tyr Ala Lys
        195                 200                 205

Leu Leu Gly Leu Leu Ala Glu Leu Arg Ser Ile Asn Glu Ala Tyr Gly
        210                 215                 220
```

```
Tyr Gln Ile Gln His Ile Gln Gly Leu Ser Ala Met Met Pro Leu Leu
225                 230                 235                 240

Gln Glu Ile Cys Ser
                245
```